US008445190B2

(12) United States Patent
Lambris et al.

(10) Patent No.: US 8,445,190 B2
(45) Date of Patent: May 21, 2013

(54) METHOD OF INHIBITING BIOMATERIAL-INDUCED PROCOAGULANT ACTIVITY USING COMPLEMENT INHIBITORS

(75) Inventors: John D. Lambris, Philadelphia, PA (US); Konstantinos Ritis, Alexandroupolis (GR)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 70 days.

(21) Appl. No.: 13/121,396

(22) PCT Filed: Sep. 29, 2009

(86) PCT No.: PCT/US2009/058745
§ 371 (c)(1),
(2), (4) Date: Jun. 7, 2011

(87) PCT Pub. No.: WO2010/039690
PCT Pub. Date: Apr. 8, 2010

(65) Prior Publication Data
US 2011/0269113 A1 Nov. 3, 2011

Related U.S. Application Data

(60) Provisional application No. 61/101,453, filed on Sep. 30, 2008.

(51) Int. Cl.
*A01N 1/02* (2006.01)
*A61M 1/34* (2006.01)

(52) U.S. Cl.
USPC .................................. 435/2; 422/44

(58) Field of Classification Search
USPC .................................. 435/2; 422/44
See application file for complete search history.

(56) References Cited

U.S. PATENT DOCUMENTS

| | | | |
|---|---|---|---|
| 6,180,370 B1 | 1/2001 | Queen et al. | |
| 6,319,897 B1 | 11/2001 | Lambris et al. | |
| 6,559,176 B1* | 5/2003 | Bassler et al. | 514/408 |
| 6,780,890 B2* | 8/2004 | Bassler et al. | 514/562 |
| 2003/0224490 A1 | 12/2003 | Dessain et al. | |
| 2006/0217530 A1 | 9/2006 | Maxwell et al. | |
| 2007/0172483 A1 | 7/2007 | Schwaeble et al. | |
| 2008/0227717 A1 | 9/2008 | Lambris et al. | |
| 2008/0233113 A1 | 9/2008 | Bansal | |
| 2011/0160636 A1* | 6/2011 | Bansal | 604/6.09 |
| 2011/0269113 A1* | 11/2011 | Lambris et al. | 435/2 |

FOREIGN PATENT DOCUMENTS

| | | |
|---|---|---|
| WO | 9913899 | 3/1999 |
| WO | 2004026328 | 4/2004 |

OTHER PUBLICATIONS

Adams et al. Hypercoagulabolity in chronic kidney disease is associated with coagulation activation but not endothelial function. *Thromb Res*; Epub ahead of print. vol. 123, Issue 2, pp. 374-380, Dec. 2008.
Agostini et al., Complement activation during hemodialysis. *J Biomater Appl*, 4; 102-22 (1989).
Ames et al., Identification of a selective nonpeptide antagonist of the anaphylatoxin C3a receptor that demonstrates anti-inflammatory activity in animal models. *Jimmunol*, 166: 6341-6348 (2001).
Appel Li Beyond (or back to) traditional risk factors: preventing cardiovascular disease in patients with chronic kidney disease. *Ann Intern Med*, 140: 60-61 (2004).
Bird et al., Single Chain Antigen-Binding Proteins, Science 242:423-426, 1988.
Bohler et al., Reduction of Granulocyte Activation During Hemodialysis with Regional Citrate Anticoagulation: Dissociation of Complement Activation and Neutropenia From Neutrophil Degranulation. *J Am Soc Nephrol*; 7: 234-241 (1996).
Burton et al., Adv. Anti-C3 Antibodies are also Commercially Available, Other C3 Inhibitors Include C3-Binding and Complement Inhibitory Secreted *S. Aureus* Extracellular Fibrinogen-Binding Protein EFB, *Immunol*, 57:191-280 (1994).
Cella et al., Tissue Factor Pathway Inhibitor (TFPI) Activity in Uremic Patients During Hemodialysis. *Thromb Res*, 81: 671-7 (1996).
Chazan et al., Long-Term Survival of Vascular Accesses in a Large Chronic Hemodialysis Population. *Nephron*, 69: 228-33 (1995).
Chenoweth De. Complement Activation During Hemodialysis: Clinical Observations, Proposed Mechanisms, and Theoretical Implications. *Artif Organs*, 9: 281-90 (1984).
Collins Aj. Cardiovascular Mortality in End-Stage Renal Disease. *Am J Med Sc.i*, 325(4): 163-167 (2003).
Craddock et al., Complement and Leukocyte-Mediated Pulmonary Dysfunction in Hemodialysis. *N Engl J Med*, 296(14): 769-774 (1977).
Craddock et al., Hemodialysis leukopenia. Pulmonary Vascular Leukostasis Resulting From Complement Activation by Dialyzer Cellophane Membranes. *J Clin Invest.*, 59(5): 879-888 (1977).
Culleton et al., Cardiovascular Disease and Mortality in a Community-Based Cohort With Renal Insufficiency. *Kidney Int*, 56: 2214-2219 (1999).

(Continued)

*Primary Examiner* — Raymond Henley, III
(74) *Attorney, Agent, or Firm* — Potter Anderson & Corroon LLP

(57) ABSTRACT

Methods for reducing or eliminating biomaterial-induced procoagulant activity in blood subjected to extracorporeal treatment that exposes the blood to the biomaterial are disclosed. The methods involve treatment of the blood, or the extracorporeal biomaterial, or both, with a complement inhibitor to inhibit C5a/C5aR-mediated tissue factor formation in the blood.

18 Claims, 7 Drawing Sheets

OTHER PUBLICATIONS

Culleton et al., Cardiovascular Disease: Risk Factors, Secular Trends, and Therapeutic Guidelines. *J Am Sac Nephrol*, 9: S5-15, (1998).

Deppisch et al., Complement Components As Uremic Toxins and Their Potential Role As Mediators of Microinflammation. *Kidney Int*, 59, Suppl 78: 271-277 (2001).

Foley Rn. Cardiac Disease in Chronic Uremia: Can It Explain the Reverse Epidemiology of Hypertension and Survival in Dialysis Patients? *Seminars in dialysis*, 17(4): 275-278 (2004).

Gasque P. Complement: a unique innate immune sensor for danger signals. *Mol, Immunol*, 41: 1089-1098 (2004).

Girardi et al., Complement C5a receptors and neutrophils mediate fetal injury in the antiphospholipid syndrome. *J. Clin, Investig.*, 112: 1644-1654 (2003).

Gorbet et al., Flow cytometric study of in vitro neutrophil activation by biomaterials. *JBiomed Mater Res*, 44: 289-97, (1999).

Gorbet et al,, Leukocyte activation and leukocyte procoagulant activities after blood contact with polystyrene and polyethylene glycol-immobilized polystyrene beads. *J Lab Clin Med*, 137: 345-55 (2001).

Gorbet et al., Material-induced tissue factor expression but not CD1 1 b upregulation depends on the presence of platelets. *JBiomed Mater Res*, 67A: 792-800 (2003).

Gorbet et al., Biomaterials-associated thrombosis: roles of coagulation factors, complement, platelets and leykocytes. *Biomaterias*, 25: 5681-5703 (2004).

Gu, et al., Construction and Expression of Mouse-Human Chimeric Antibody SZ-51 Specific for Activated Platelet P-Selectin, Thrombosis and Hematocyst, vol. 77, pp. 755-759 (1997).

Guo et al., Role of C5a in inflammatory responses. *Ann Rev Immunol*, 23: 821-852 (2005).

Hammel et al., A structural basis for complement inhibition by *Staphylococcus aureus*, Nat. Immunol., vol. 8, pp. 430-437 (2007).

Hong et al., A new in vitro model to study interaction between whole blood and biomaterials. Studies of platelet and coagulation activation and the effect of aspirin. *Biomaterials*, 20: 603-11 (1999).

Horl et al., Plasma levels of main granulocyte components during hemodialysis. Comparison of new and reused dialyzers. *Am J Nephrol*, 10 (1): 53-57 (1990).

Houston et al., Protein engineering of antibody binding sites: recovery of specific activity in an anti-..., Proc. Natl. Acad. Sci. USA, vol. 85, pp. 5879-5883 (1988).

Jofre et al., Inflammatory syndrome in patients on hemodialysis. *JAm Soc Nephrol*, 17: S274-S280 (2006).

Jozsi et al., Characterization of factor H-related cell membrane molecules expressed by human B lymphocytes and neutrophil granulocytes. *Immunology Letters*, 77: 55-62, (2001).

Jungers et al., Incidence of Atherosclerotic Arterial Occlusive Accidents in Predialysis and Dialysis Patients: A Multicentric Study in the Ile de France district. *Nephrol Dial Transplant*, 14: 898-902 (1999).

Kambas et al., C5a and TNF-Alpha Up-Regulate The Expression of Tissue Factor in Intra-Alveolar Neutrophils of Patients With the Acute Respiratory Distress Syndrome. *JImmunol*, 180 (11): 7368-75 (2008).

KAPLOW_et al., Profound Neutropenia During the Early Phase of Hemodialysis. *JAMA*, 203(13): 1135-1137 (1968).

Kario et al., Increased Tissue Factor Pathway Inhibitor Levels in Uremic Patients on Regular Hemodialysis. *Thromb Haemost*; 71; 275-9 (1994).

Kaysen Ga. The microinflamxnatory state in uremia: causes and potential consequences. *J Am Soc Nephrol*, 12: 1549-1557 (2001).

Krutzik et al., Coordinate Analysis of Murine Immune Cell Surfacemarkers and Intracellular Phosphoproteins by Flow Cytometry. *JImmunol*, 175: 2357-65 (2005).

Lappegard et al., Differential Effect of Heparin Coating and Complement Inhibition on Artificial Surface-Induced Eicosanoid Production. *Ann Thorac Surg*, 79: 917-923 (2005).

Lee et al., Identification and Characterization of the C3 Binding Domain of the *Staphylococcus Aureus* Extracellular Fibrinogen-Binding Protein (Efb), J. Biol. Chem., vol. 279, pp. 50710-50716 (2004).

Livak et al., Analysis of relative gene expression data using real time quantitative PCR and the $2^{-DDCT}$ method. *Methods*, 25: 402-408 (2001).

Lowrie et al., Death risk in hemodialysis patients: The Predictive Value of Commonly Measured Variables and an Evaluation of Death Rate Differences Between Facilities. *Am JKidney Dis*, 15: 458-482 (1990).

Mackman et al,, Role of the Extrinsic Pathway of Blood Coagulation in Hemostasis and Thrombosis. *Arterioscler Thromb Vasc Biol*, 27: 1687-1693 (2007).

Maderna et al., Serum from Hemodialysis Patients Inhibits Basal and Cytokine-Stimulated Tissue Factor Expression in Vitro, *J Am Soc Nephrol*, 10: 2403-2406 (1999).

Mallik et al., Design and NMR Characterization of Active Analogs of Compstatin Containing Non-Natural Amino Acids. *J Med Chem*, 48: 274-286 (2005).

Mastellos et al., A Novel Role of Complement: Mice Deficient in the Fifth Component of Complement (C5) Exhibit Impaired Liver Regeneration. *J Immunol*, 166: 2479-2486 (2001).

A 5' Maugeri et al, Human polymorphonuclear leukocytes produce and express functional tissue factor upon stimulation. *J Thromb Haemost*, 4: 1323-30 (2006).

Morikis et al Design, Structure, Function and Application of Compstatin, 235-246 (1999).

Nilsson et al., Compstatin inhibits complement and cellular activation in whole blood in two models of extracorporeal circulation. *Blood*, 92: 1661-1667 (1998).

Nilsson et al., the role of complement in biomaterial-induced inflammation. *Mol Immunol*, 44: 82-94 (2007).

Proctor et al., Transdermal Pharmacology of Small Molecule Cyclic C5a Antagonists, Adv. Exp. Med. Biol., vol. 586, pp. 329-345 (2006).

Rafail et al,, Leptin Induces the Expression of Functional Tissue Factor in Human Neutrophils and Peripheral Blood Mononuclear Cells Through JAK2-Dependent Mechanisms and TNFalpha Involvement. *Thromb Res*,122(3): 366-75 (2008).

Redecha_et al., Tissue Factor: A Link Between C5a and Neutrophil Activation in Antiphospholipid Antibody Induced Fetal Injury. *Blood*; 110(7): 2423-31 (2007).

Ritis et al., A Novel C5a Receptor-Tissue Factor Cross-Talk in Neutrophils Links Innate Immunity to Coagulation Pathways. *JImmunol*, 177: 4794-4802 (2006).

Rosamond Wd et al., Trends in the Incidence of Myocardial Infarction and in Mortality due to Coronary Heart Disease. *N Engl J Med*,339: 861-867 (1998).

Rosenkranz et al., Novel C5a-Dependent Mechanism of Neutrophil Stimulation by Bioincompatible Dialyzer Membranes. *J Am Soc Nephrol*, 10: 128-135 (1999).

Sahu et al., Inhibition of Human Complement by a C3-binding Peptide Isolated from a Phage-Displayed Random Peptide References List, *JImmunol*, 157: 884-891 (1996).

Sarnak et al., Kidney Disease as a Risk Ractor for Development of Cardiovascular Disease. A Statement from the American Heart Association Councils on Kidney in Cardiovascular Disease, High Blood Pressure Research, Clinical Cardiology, and Epidemiology and Prevention. Hypertension., 42: 1050-1065 (2003).

Sarnak et al., Epidemiology of cardiac disease in dialysis patients, *Semin Dial*, 12: 6976 (1999).

Schenone et al., The Blood Coagulation Cascade. *Curr Opin Hematol*, 11: 272-277 (2004).

Schmaldienst et al., Degranulation of Polymorphonuclear Leukocytes by dialysis Membranes—the Mystery Clears up? *Nephrol Dial Transplant*, 15: 1909-1910 (2000).

Skubitz Km, Craddock Pr. Reversal of Hemodialysis Granulocytopenia and Pulmonary Leukostasis. a Clinical Manifestation of Selective Downregulation of Granulocyte Responses to C5adesarg. *J Clin Invest*, 67: 1383-1391 (1981).

Smits et al., Coagulation and Hemodialysis Access Thrombosis. *Nephrol Dial Transplan*, 15: 1755-1760 (2000).

Stenvinkel et al., Emerging Biomarkers for Evaluating Cardiovascular Risk in the Chronic Kidney Disease Patient: how do new Pieces fit Into the Uremic Puzzle? *Clin J Am Soc Nephrol*; 3: 505-521 (2008).

Szotowski et al., Procoagulant Soluble Tissue Factor is Released From Endothelial Cells in Response to Inflammatory Cytokines. *Circ Res*, 96: 1233-1239. (2005).

Tuszynski et al,, Thrombospondin Promotes Platelet Aggregation, Blood, vol. 72, pp. 109-115 (1988).

US Renal Data System, Causes of Death in ESRD. *Am J Kidney Dis*, 34(suppl 1): S87-S94 (1999).

US Renal Data System. USRDS 2001 Annual Data Report: Atlas of end-stage Renal Disease in the United States, Bethesda (MD): National Institutes of Health, National Institute of Diabetes and Digestive and Kidney Diseases; 2001.

Ward PA, The Dark Side of C5a in Sepsis. *Nat Rev Immunol*, 4: 133-142 (2004).

Wolberg et al., Mechanisms of Autoantibody-Induced Monocyte Tissue Factor Expression. *Thromb Res*,114: 391-396 (2004).

Wright et al., Genetically Engineered Antibodies: Progress and Prospects, Critical Rev. in Immunol. 12(3,4);125-168) (1992).

Yeun Jy et al., C-reactive Protein Predicts all Cause and Cardiovascular Mortality in Hemodialysis Patients. *Am JKidney Dis*, 35: 469-476 (2000).

Zemanova et al., Tissue Factor, Its Inhibitor, and the Thrombogenicity of Two New Synthetic Membranes. *Artificial Organs*, 29(8): 651-657 ((2005).

Zernecke A et al., Protective role of CXC Receptor 4/CXC Ligand 12 Unveils the Importance of Neutrophils in Atherosclerosis. *Circ Res*, 102: 209-217 (2008).

Zimmermann et al., Inflammation Enhances Cardiovascular Risk and Mortality in Hemodialysis Patients. *Kidney Int.*, 55: 648-658 (1999).

International Search Report filed Sep. 29, 2009, Application No. PCT/US09/58745, mailed Nov. 30, 2009.

U.S. Appl. No. 13/121,396, Notice of Allowance and Fee(s) Due, mailed Oct. 16, 2012.

\* cited by examiner

A

B

A

B

C

A

B

A

B

C

METHOD OF INHIBITING BIOMATERIAL-INDUCED PROCOAGULANT ACTIVITY USING COMPLEMENT INHIBITORS

Pursuant to 35 U.S.C. §202(c), it is acknowledged that the United States government may have certain rights in the invention described herein, which was made in part with funds from the National Institutes of Health under Grant Nos. AL068730 and GM-62134.

FIELD OF THE INVENTION

This invention relates to the field of extracorporeal treatment of blood, such as hemodialysis. Methods for reducing or eliminating biomaterial-induced procoagulant activity in blood subjected to extracorporeal treatment that exposes the blood to the biomaterial are provided. The methods involve treatment of the blood, or the extracorporeal biomaterial, or both, with a complement inhibitor to inhibit C5a/C5aR-mediated tissue factor formation in the blood.

BACKGROUND OF THE INVENTION

Various publications, including patents, published applications, technical articles and scholarly articles are cited throughout the specification. Each of these cited publications is incorporated by reference herein, in its entirety. Full citations for publications not cited fully within the specification are set forth at the end of the specification.

Thrombotic cardiovascular complications represent the leading cause of death among patients with end-stage renal disease (ESRD) and account for more than half of death in such patients. The well-documented high mortality rate in ESRD is especially prominent in patients on dialysis. Since the cardiovascular death rate in dialysis patients is unaccepted high (almost 40-fold higher than in the general population), great scientific interest has gathered on this topic and intense efforts aim 1n attenuating this phenomenon. In addition, vascular-access thrombotic events in hemodialysis patients constitute a major morbidity cause. However, although spectacular achievements have been accomplished in reducing cardiovascular death and thrombotic events in the general population through better control of traditional risk factors, no such trend has been detected for patients with ESRD and results are far from optimal. This might be due to the fact that traditional risk factors (such as hypertension and hyperlipidemia) are less predictive of thrombotic events in ESRD patients than in the general population, while markers of inflammation predict all cause and cardiovascular mortality in hemodialysis patients, underlining the significant role of inflammation in the atherothrombotic process.

Inflammation and thrombosis are linked in certain clinical models. Biomaterials are known inflammatory agonists and induce leukocytes and complement activation [15-19]. Neutrophils and complement are key mediators of innate immunity and play a pivotal role in the inflammatory response to various stimuli [20]. Thus, chronic hemodialysis in ESRD patients is considered as a major contributor for atherosclerosis through chronic inflammatory activation [21, 22]. In addition, TF extrinsic pathway plays the main in vivo role for coagulation triggering [23]. However, the mechanisms of TF regulation in coagulant process in such patients remain elusive. Different inflammatory agonists are responsible for TF induction in monocytes and activated endothelial cells. Recently it has been reported that neutrophils are able to produce functional TF through C5a/C5aR, thus suggesting that this novel pathway may be implicated in different clinical models [24].

As can be seen from the foregoing discussion, cardiovascular and/or vascular-access thrombotic events are very prominent in ESRD patients, especially those on dialysis. Although several mechanisms have been proposed, no substantial progress in reducing morbidity and mortality has been accomplished. Thus, there is a need in the art to identify and develop new methods for alleviating these unwanted and dangerous side-effects of hemodialysis and other extracorporeal treatments. This invention addressed those needs.

SUMMARY OF THE INVENTION

One aspect of the invention provides a method for reducing or eliminating biomaterial-induced procoagulant activity in blood subjected to extracorporeal treatment that exposes the blood to the biomaterial. The method comprises treating the blood, or the biomaterial, or both, with a complement inhibitor in an amount effective to reduce or prevent C5a/C5aR-mediated tissue factor (TF) formation, thereby reducing or eliminating the biomaterial-induced procoagulant activity in the blood. Any inhibitor of the complement cascade leading to the formation or activity of C5a or the C5a receptor (C5aR) can be used in the method. In various embodiments, the complement inhibitor comprises one or more of a C5a inhibitor, a C5aR inhibitor, a C3 inhibitor, a factor D inhibitor, a factor B inhibitor, a C4 inhibitor, a C1q inhibitor, or any combination thereof. For example, suitable C5a inhibitors or C5aR inhibitors include but are not limited to acetyl-Phe-[Orn-Pro-D-cyclohexylalanine-Trp-Arg] (PMX-53), PMX-53 analogs, neutrazumab, TNX-558, eculizumab, pexelizumab or ARC1905, or any combination thereof. Suitable C3 inhibitors include but are not limited to is compstatin, a compstatin analog, a compstatin peptidomimetic, a compstatin derivative, or any combinations thereof.

In one embodiment, the extracorporeal treatment of blood comprises hemodialysis, and the biomaterial comprises hemodialysis filter fibers. This embodiment is suitable for treatment of individuals suffering from renal disease, particularly end stage renal disease (ESDR).

In embodiments comprising treatment of the blood, the blood can be contacted with the complement inhibitor prior to and/or during the extracorporeal treatment. In embodiments comprising treatment of the biomaterial, the biomaterial can contacted with the complement inhibitor prior to its use in the extracorporeal treatment. Such prior contacting can be performed immediately prior to use, or at some period of time prior to use, within the stability and activity parameters of the selected complement inhibitor(s).

In other embodiments, the complement inhibitor treatment is used together or concurrently with, or sequentially before or after, at least one other anti-coagulant or anti-inflammatory treatment of the blood or of the individual.

Another aspect of the invention features a kit, or article of manufacture, comprising a complement inhibitor and a biomaterial for use in an extracorporeal treatment device, and, optionally, instructions for using the complement inhibitor in a method such as the one described above. In one embodiment, the biomaterial comprises a hemodialysis filtration material.

Another aspect of the invention features an extracorporeal treatment device that includes a complement inhibitor-treated biomaterial, or a biomaterial adapted for or amenable to treatment with a complement inhibitor. In one embodiment, the device is a hemodialysis unit.

Other features and advantages of the invention will be understood by reference to the drawings, detailed description and examples that follow.

Figure 1:
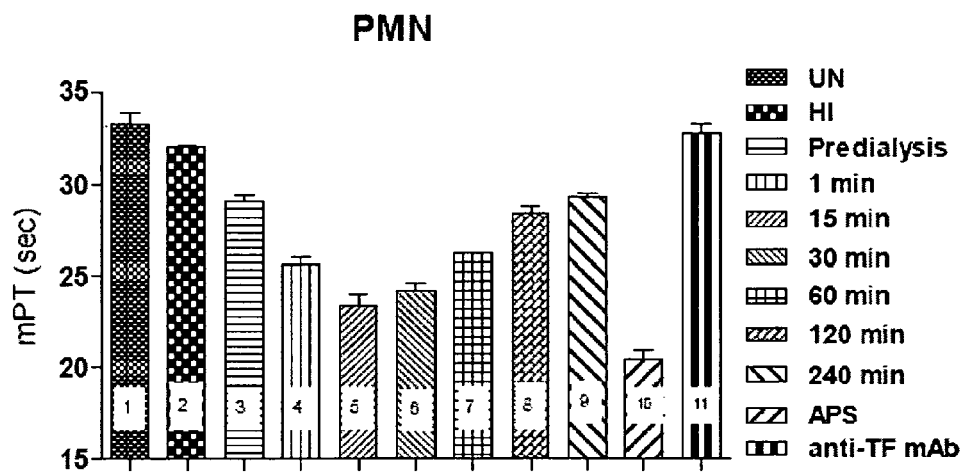
FIG. 1: TF-dependent procoagulant properties of ESRD serum. A: The supernatants from PMNs incubated with predialysis serum (bar 3) showed higher procoagulant activity than unstimulated neutrophils (UN: bar 1) as well as cells incubated with sera of healthy subjects (HI: bar 2). Supernatants after incubation with sera from the initial phase of hemodialysis caused notably low mPT values (bar 4) that reached a peak at 15-30 min (bars 5, 6) before gradually returning to predialysis status at 240 min (bar 9). Supernatants from neutrophils incubated with APS serum served as positive controls (bar 10), while the addition of neutralizing anti-TF mAb in culture supernatants inverts completely the observed procoagulant effect (bar 11). B: Procoagulant activity of PBMC culture supernatants induced by ESRD sera was in concordance with PMNs and demonstrated a similar time and TF-dependent pattern (Predialysis: bar 3—28.25±0.35 sec, $p<0.05$ vs. bars: 1—32.90±0.28 sec and 2—32.17±0.23 sec, 15 min: 23.07±0.37 sec, 30 min: 24.30±0.42 sec, anti-TF mAb: 32.85±0.21 sec, $p<0.01$ compared to bars 1 and 2).
Figure 1:
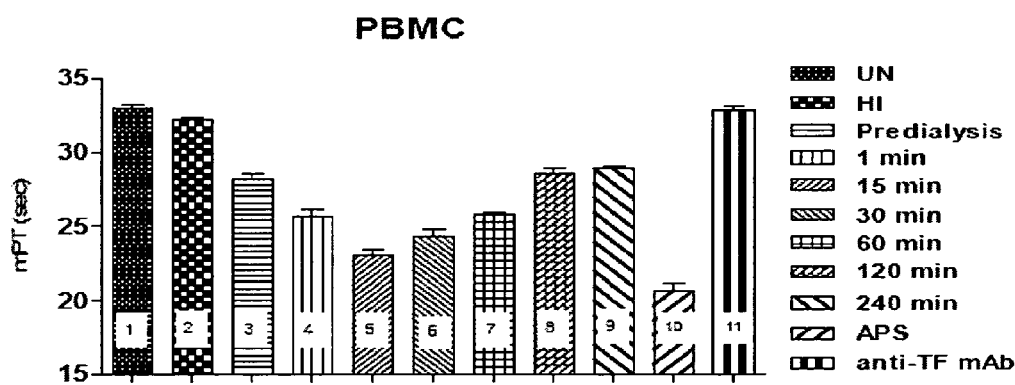

4: Involvement of the complement pathway in the procoagulant properties of ESRD serum. A: ESRD serum taken at 15 to 30 min of hemodialysis was treated with Compstatin (15 μM-30 min) and the procoagulant effect in healthy donor's PMNs (N=6) was completely attenuated, (bar 4: 30.29±0.42, $p<0.001$ compared to bar 3: 22.96±0.22), returning the mPT values near to those of controls (bar 1: 31.96±0.21), reversing even the predialysis TF activity (bar 2: 28.45±0.35). Similarly, preincubated PMNs with a highly selective C5aR antagonist (10 μM-30 min) completely reduced their procoagulant activity (bar 5: 31.65±0.28, $p<0.001$ compared to bar 3). In contrast, both a selective C3aR antagonist (10 μM-30 min) and a non-active linear analogue of compstatin had no effect on mPT values (bars 6, 7: 22.99±0.26 and 24.16±0.23, respectively; p: n.s. vs. bar 3). B: According to rt RT-PCR data, a significant reduction of TF mRNA expression, after Compstatin addition was observed (bar 2: 2.79 fold decrease, average DCt 9.40±0.43 vs. PMNs incubated with activated serum-bar 1: 7.92±0.29, $p<0.01$). C5aR antagonism also notably attenuated TF expression levels (bar 3: 2.14 fold decrease, average DCt 9.02±0.62 vs. bar 1, $p<0.01$).

Figure 5:
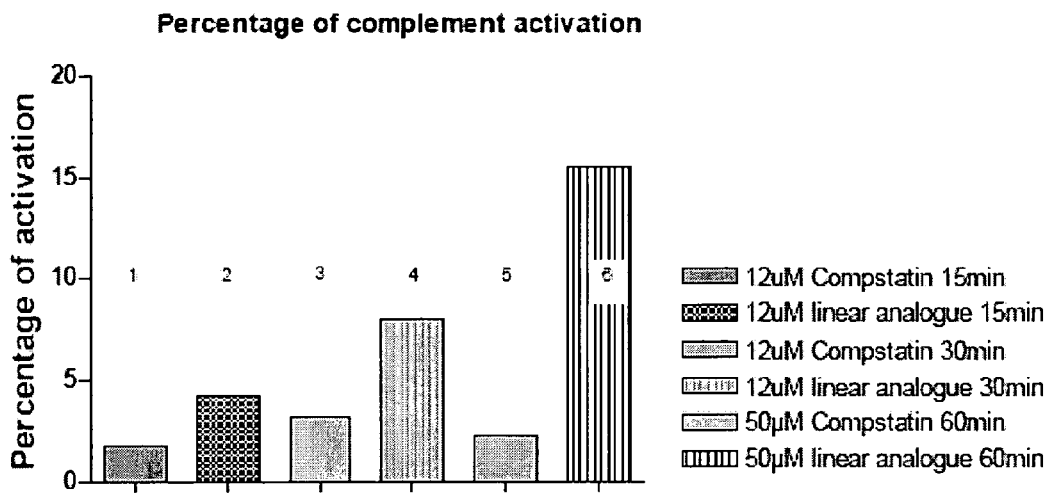
Figure 5:
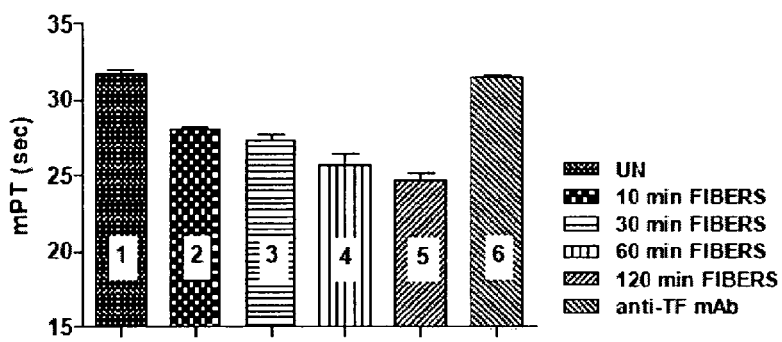
Figure 5:
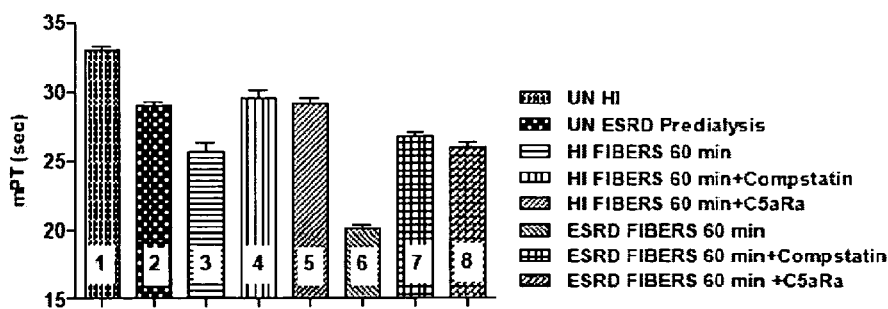

FIG. 5: Hemodialysis filter fibers induce in vitro TF dependent procoagulant properties in both ESRD and healthy serum through complement activation. A: 300 ul of plasma was incubated with 15 mg fibers in glass vials for different time intervals in the presence of different concentration of 4(1 MeW) compstatin or inactive linear compstatin. C3b generation was detected by ELBA. CVF-activated plasma was used as a standard for 100% complement activation. The percentage of complement activation is depicted in the diagram. B: Serum from healthy donors was preincubated with hollow fibers from polysulfone hemodialysis filters at different time periods (10, 30, 60 & 120 min). PMNs were incubated with the pretreated serum and their supernatants were assayed for TF with mPT. A time-dependent procoagulant activity was observed (bar 2: 28.06±0.21, 3: 27.32±0.39, 4: 25.65±0.78, 5: 24.67±0.47, $p<0.01$ compared to bar 1: 31.81±0.28), which was blocked by the addition of anti-TF mAb in supernatants showing the highest procoagulant effect (bar 6: 31.49±0.12, $p<0.05$ compared to bar 5). C: Predialysis ESRD serum pre-incubated for 60 min with filter fibers, induced stronger procoagulant activity in PMN culture supernatants compared to when healthy serum was used (bars 3: 25.65±0.78, 6: 20.06±0.35, $p<0.01$ compared to bars 1: 33.12±0.25, 2: 29.07±0.33, respectively). Inhibitions with compstatin or C5aR antagonist, in both pre-treated sera, elucidated that the observed TF-dependent procoagulant activity was complement mediated (bars 4: 29.60±0.57, 5: 29.15±0.49 & 7: 26.85±0.21, 8: 26.05±0.35, $p<0.01$ compared to bars 3 and 6, respectively).

Figure 6:
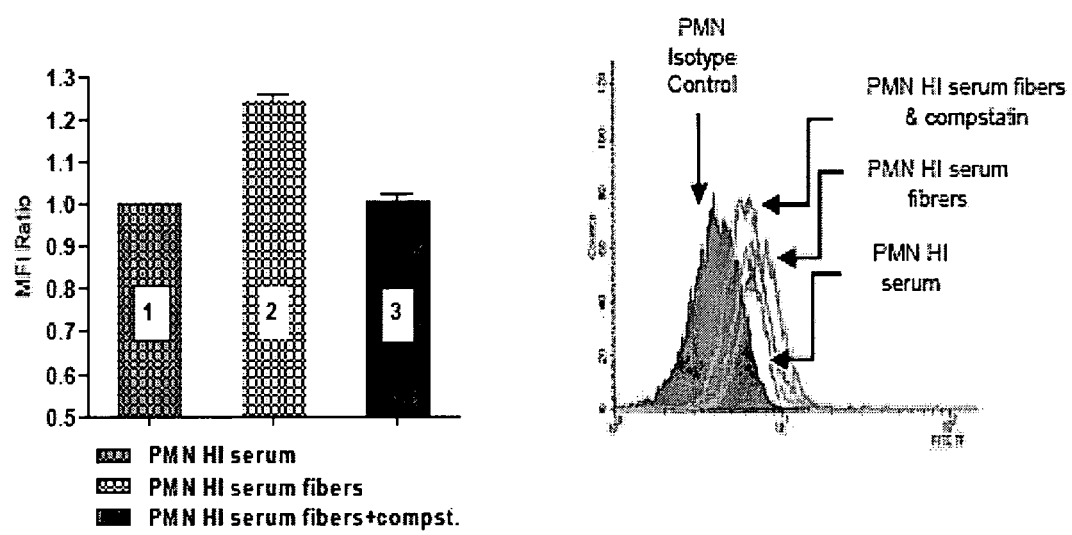
Figure 6:
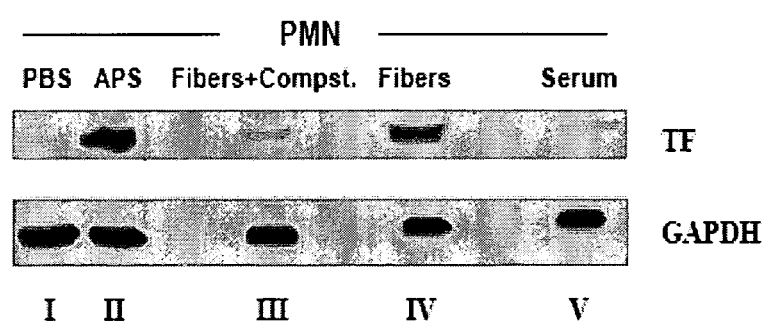

FIG. 6: Protein analysis confirms complement's role in TF expression by healthy PMNs in vitro. Cultured PMNs with activated or blocked healthy serum were analysed for TF antigen presence. A: MFI fold expression revealed an increase of intracellular TF protein expression (bar 2), while Compstatin promoted the inhibition of the effect (bar 3). B: Western blot analysis results come in par with those of flow cytometry (neutrophils incubated with: untreated serum (V), treated with filter fibers (IV) and serum blocked with Compstatin (III); extracts from PMNs incubated with PBS (I) and APS serum (II) were used as negative and positive controls, respectively (representative data from four independent experiments).

Figure 7:
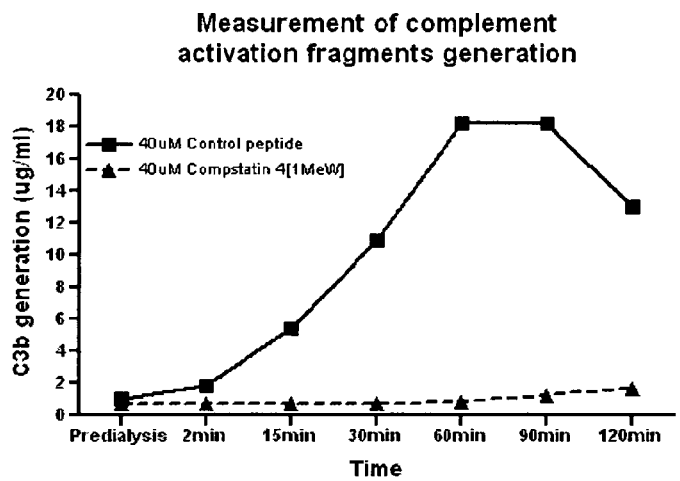
Figure 7:
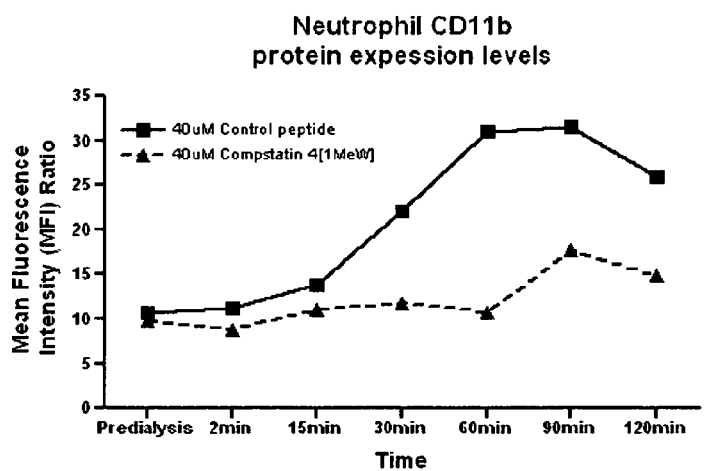
Figure 7:
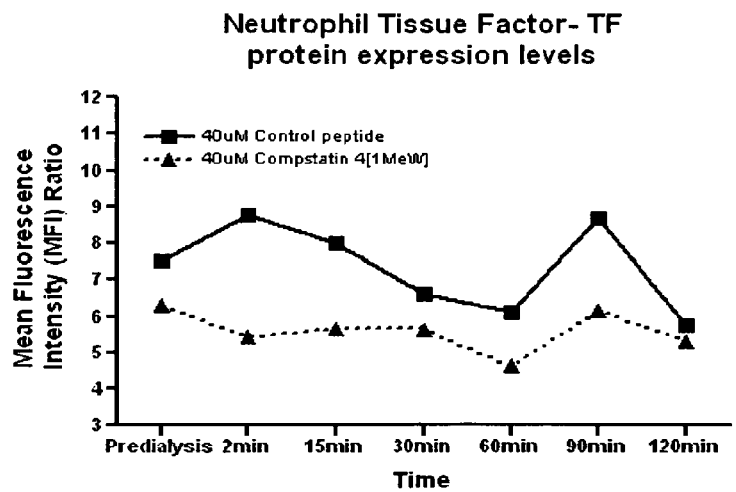

FIG. 7. Complement activation during hemodialysis simulation is reduced or prevented by a compstatin analog. Analysis of complement activation in plasma samples collected at several time points during simulation of hemodialysis procedure in blood treated with 40 uM of compstatin analog [4 MeW] or an inactive analog. A: ELISA detection of complement activation fragment C3b using a C3-9 mAB. B: Detection of cellular cascade activation by flow cytometry after surface staining of blood neutrophils for CD11b. C: Detection of coagulation cascade activation by flow cytometry after intracellular staining of blood neutrophils for tissue factor (TF).

DETAILED DESCRIPTION OF ILLUSTRATIVE EMBODIMENTS

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

As used herein, a "complement inhibitor" is a molecule that prevents or reduces activation and/or propagation of the complement cascade that results in the formation of C5a or signaling through the C5a receptor. A complement inhibitor can operate on one or more of the complement pathways, i.e., classical, alternative or lectin pathway.

As used herein, a "C3 inhibitor" is a molecule or substance that prevents or reduces the cleavage of C3 into C3a and C3b.

As used herein, a "C5a inhibitor" is a molecule or substance that prevents or reduces the activity of C5a.

As used herein, a "C5aR inhibitor" is a molecule or substance that prevents or reduces the binding of C5a to the C5a receptor.

As used herein, a "C3aR inhibitor" is a molecule or substance that prevents or reduces binding of C3a to the C3a receptor.

As used herein, a "factor D inhibitor" is a molecule or substance that prevents or reduces the activity of Factor D.

As used herein, a "factor B inhibitor" is a molecule or substance that prevents or reduces the activity of factor B.

As used herein, a "C4 inhibitor" is a molecule or substance that prevents or reduces the cleavage of C4 into C4b and C4a.

As used herein, a "C1q inhibitor" is a molecule or substance that prevents or reduces C1q binding to antibody-antigen complexes, virions, infected cells, or other molecules to which C1q binds to initiate complement activation.

Any of the inhibitors described herein may comprise antibodies or antibody fragments, as would be understood by the person of skill in the art.

"Treating" refers to any indicia of success in the treatment or amelioration of the disease or condition. Treating can include, for example, reducing or alleviating the severity of one or more symptoms of the disease or condition, or it can include reducing the frequency with which symptoms of a disease, defect, disorder, or adverse condition, and the like, are experienced by a patient. "Treating" can also refer to reducing or eliminating a condition of a part of the body, such as a cell, tissue or bodily fluid, e.g., blood.

"Preventing" refers to the partial or complete prevention of the disease or condition in an individual or in a population, or in a part of the body, such as a cell, tissue or bodily fluid (e.g., blood). The term "prevention" does not establish a requirement for complete prevention of a disease or condition in the entirety of the treated population of individuals or cells, tissues or fluids of individuals.

The term "treat or prevent" is sometimes used herein to refer to a method that results in some level of treatment or amelioration of the disease or condition, and contemplates a range of results directed to that end, including but not restricted to prevention of the condition entirely.

A "prophylactic" treatment is a treatment administered to a subject (or sample) who does not exhibit signs of a disease or condition, or exhibits only early signs of the disease or condition, for the purpose of decreasing the risk of developing pathology associated with the disease or condition. This term may be used interchangeably with the term "preventing," again with the understanding that such prophylactic treatment or "prevention" does not establish a requirement for complete prevention of a disease in the entirety of the treated population of individuals or tissues, cells or bodily fluids.

As used herein, a "therapeutically effective amount" or simply an "effective amount" is the amount of a composition sufficient to provide a beneficial effect to the individual to whom the composition is administered, or who is otherwise treated using a method involving the composition.

The term "extracorporeal treatment" as used herein refers generally to treatment or manipulation of cells, tissues or bodily fluids that have been removed from an individual and are thereafter returned to the same individual or to another individual. Examples of extracorporeal treatments include, but are not limited to, extracorporeal shunting of blood during surgical procedures, for example, hemodialysis, and cell or tissue transplantation, to name a few.

The term "biomaterials" as used herein refers to components of equipment, devices or articles that come into contact with, and particularly that perform a function in connection with, the cells, tissues or biological fluids being subjected to the extracorporeal treatment. One example of a biomaterial is the filter material in a hemodialysis unit.

It is understood that any and all whole or partial integers between any ranges set forth herein are included herein.

Description

Cardiovascular and/or vascular-access thrombotic events are very prominent in ESRD patients, especially those on dialysis. Although several mechanisms have been proposed, no substantial progress in reducing morbidity and mortality has been accomplished. Biomaterials used in hemodialysis are known complement activators, and previous studies reported a link between complement-neutrophil crosstalk and thrombosis through Tissue Factor (TF) pathway in patients with antiphospholipid syndrome [24]. The present invention springs in part from the inventors demonstration of the implication of a similar mechanism in the hyper-coagulant state of dialysis-ESRD patients.

As described in greater detail herein, after stimulation of healthy blood leukocytes with ESRD patient serum, TF-dependent procoagulant activity of supernatants was observed, which was inhibited by specific anti-TF mAb. Moreover, the ex vivo ability of ESRD serum to induce TF was associated with TF expression in RNA and protein levels from patient leukocytes. This TF induction from patient serum was shown to be complement dependent, in particular C5a mediated, as it was demonstrated in ELISA analysis and complement blockade studies using the complement inhibitor compstatin and a selective C5a-Receptor antagonist. Furthermore, a time dependent manner of complement activation and TF expression during the hemodialysis course was identified, thus leading to prothrombotic activity reaching a peak at $15^{th}$-$30^{th}$ min of hemodialysis. Finally, in vitro experiments using healthy and ESRD serum confirmed the ability of dialysis biomaterials to induce the C5a activation—TF expression process by blood leukocytes.

Thus, the inventors have identified hemodialysis-ESRD patients as a clinical disorder where the C5aR/blood leukocytes crosstalk is strongly implicated with subsequent TF pathway triggering. This pathway functions as an additional inducer of thrombotic events, and thus indicates novel therapeutic targets and interventions, as described below. The inventors have further demonstrated that extracorporeal treatment of blood during hemodialysis reduces or prevents complement activation, as evidenced by several factors, including TF production in neutrophils.

Accordingly, one aspect of the present invention features a method for reducing or eliminating biomaterial-induced procoagulant activity in blood subjected to extracorporeal treatment that exposes the blood to the biomaterial. The method comprises treating the blood, or the biomaterial, or both, with a complement inhibitor in an amount effective to reduce or prevent C5a/C5aR-mediated tissue factor (TF) formation, thereby reducing or eliminating the biomaterial-induced procoagulant activity in the blood. The method is particularly applicable to hemodialysis the treatment of hemodialysis filter fibers, for the treatment of individuals suffering from renal disease, particularly end stage renal disease (ESDR).

As mentioned above, a "complement inhibitor" is a molecule that prevents or reduces activation and/or propagation of the complement cascade that results in the formation of C5a or signaling through the C5a receptor, also referred to herein as "C5a activity". A complement inhibitor can operate on one or more of the complement pathways, i.e., classical, alternative or lectin pathway.

Any inhibitor of C5a formation or activity may be used in the method of the invention. Inhibition of C5a formation or activity may be accomplished in a variety of ways. For instance, C5a activity may be inhibited directly by preventing or significantly reducing the binding of C5a to its receptor, C5aR. A number of C5aR inhibitors are known in the art. Acetyl-Phe-[Orn-Pro-D-cyclohexylalanine-Trp-Arg] (AcF[OPdChaWR]; PMX-53; Peptech) is a small cyclic hexapeptide that is a C5aR antagonist and is exemplified herein. Analogs of PMX-53 (e.g., PMX-201 and PMX-205) that also function as C5aR antagonists are also available (see for instance Proctor et al., 2006, Adv Exp Med. Biol. 586:329-45 and U.S. Pat. Pub. No. 20060217530). Neutrazumab (G2 Therapies) binds to C5aR, thereby inhibiting binding of C5a to C5aR. Neutrazumab (G2 Therapies) binds to extracellular loops of C5aR and thereby inhibits the binding of C5a to C5aR. TNX-558 (Tanox) is an antibody that neutralized C5a by binding to C5a.

C5a activity may also be inhibited by reducing or preventing the formation of C5a. Thus, inhibition of any step in the complement cascade which contributes to the downstream formation of C5a is expected to be effective in practicing the invention. Formation of C5a may be inhibited directly by inhibiting the cleavage of C5 by C5-convertase. Eculizumab (Alexion Pharmaceuticals, Cheshire, Conn.) is an anti-C5 antibody that binds to C5 and prevents its cleavage into C5a and C5b. Pexelizumab, an scFv fragment of Eculizumab, has the same activity. Similarly, ARC1905 (Archemix), an anti-05 aptamer, binds to and inhibits cleavage of C5, inhibiting the generation of C5b and C5a.

In another embodiment, formation of C5a is reduced or prevented through the use of a C3 inhibitor. This is a preferred embodiment of the invention, because it also inhibits C3a signaling through the C3a receptor, thereby providing a dual therapeutic effect. Preferably, the C3 inhibitor is compstatin or a compstatin analog, derivative, aptamer or peptidomimetic. Compstatin is a small molecular weight disulfide bonded cyclic peptide having the sequence Ile-Cys-Val-Val-Gln-Asp-Trp-Gly-His-His-Arg-Cys-Thr (SEQ ID NO. 1). Examples of compstatin analogs, derivatives and peptidomimetics are described in the art. See, for instance, U.S. Pat. No. 6,319,897, WO/1999/013899, WO/2004/026328, and Morikis et al (1999, "Design, Structure, Function and Application of Compstatin" in Bioactive Peptides in Drug Discovery and Design: Medical Aspects, Matsoukas et al., eds., IOS Press, Amsterdam NL).

An exemplary compstatin analog comprises a peptide having a sequence: Xaa1-Cys-Val-Xaa2-Gln-Asp-Trp-Gly-Xaa3-His-Arg-Cys-Xaa4 (SEQ ID NO. 2); wherein:

Xaa1 is Ile, Val, Leu, Ac-Ile, Ac-Val, Ac-Leu or a dipeptide comprising Gly-Ile;

Xaa2 is Trp or a peptidic or non-peptidic analog of Trp;

Xaa3 is His, Ala, Phe or Trp;

Xaa4 is L-Thr, D-Thr, Ile, Val, Gly, or a tripeptide comprising Thr-Ala-Asn, wherein a carboxy terminal —OH of any of the L-Thr, D-Thr, Ile, Val, Gly or Asn optionally is replaced by —NH$_2$; and the two Cys residues are joined by a disulfide bond. Xaa1 may be acetylated, for instance, Ac-Ile. Xaa2 may be a Trp analog comprising a substituted or unsubstituted aromatic ring component. Non-limiting examples include 2-napthylalanine, 1-naphthylalanine, 2-indanylglycine carboxylic acid, dihydrotryptophan or benzoylphenylalanine.

Another exemplary compstatin analog comprises a peptide having a sequence: Xaa1-Cys-Val-Xaa2 Gln-Asp-Xaa3 Gly Xaa4-His-Arg-Cys-Xaa5 (SEQ ID NO. 3); wherein:

Xaa1 is Ile, Val, Leu, Ac-Ile, Ac-Val, Ac-Leu or a dipeptide comprising Gly-Ile;

Xaa2 is Trp or an analog of Trp, wherein the analog of Trp has increased hydrophobic character as compared with Trp, with the proviso that, if Xaa3 is Trp, Xaa2 is the analog of Trp;

Xaa3 is Trp or an analog of Trp comprising a chemical modification to its indole ring wherein the chemical modification increases the hydrogen bond potential of the indole ring;

Xaa4 is His, Ala, Phe or Trp;

Xaa5 is L-Thr, D-Thr, Ile, Val, Gly, a dipeptide comprising Thr-Asn or Thr-Ala, or a tripeptide comprising Thr-Ala-Asn, wherein a carboxy terminal —OH of any of the L-Thr, D-Thr, Ile, Val, Gly or Asn optionally is replaced by —$NH_2$; and the two Cys residues are joined by a disulfide bond. The analog of Trp of Xaa2 may be a halogenated tryptophan, such as 5-fluoro-1-tryptophan or 6-fluoro-1-tryptophan. The Trp analog at Xaa2 may comprise a lower alkoxy or lower alkyl substituent at the 5 position, e.g., 5-methoxytryptophan or 5-methyltryptophan. In other embodiments, the Trp analog at Xaa2 comprises a lower alkyl or a lower alkenoyl substituent at the 1 position, with exemplary embodiments comprising 1-methyltryptophan or 1-formyltryptophan. In other embodiments, the analog of Trp of Xaa3 is a halogenated tryptophan such as 5-fluoro-1-tryptophan or 6-fluoro-1-tryptophan.

Other C3 inhibitors include vaccinia virus complement control protein (VCP) and antibodies that specifically bind C3 and prevent its cleavage. Anti-C3 antibodies useful in present invention can be made by the skilled artisan using methods known in the art. See, for instance, Harlow, et al. (1988, In: Antibodies, A Laboratory Manual, Cold Spring Harbor, N.Y.), Tuszynski et al. (1988, *Blood,* 72:109-115), U.S. patent publication 2003/0224490, Queen et al. (U.S. Pat. No. 6,180,370), Wright et al., (1992, *Critical Rev. in Immunol.* 12(3,4):125-168), Gu et al. (1997, *Thrombosis and Hematocyst* 77(4):755-759) and Burton et al., (1994, *Adv. Immunol.* 57:191-280). Anti-C3 antibodies are also commercially available. Other C3 inhibitors include C3-binding and complement inhibitory secreted *S. aureus* extracellular fibrinogen-binding protein Efb (Lee et al., 2004, *J. Biol. Chem.* 279: 50710-50716) and the Efb homologous protein, Ehp (Hammel et al., 2007, *J. Biol. Chem.* 282: 30051-30061).

In other embodiments, formation of C3a or C5a is reduced or prevented through the use of an inhibitor of complement activation prior C3 cleavage, e.g., in the classical or lectin pathways of complement activation. Non-limiting examples of such inhibitors include, but are not limited to: (1) factor D inhibitors such as diisopropyl fluorophosphates and TNX-234 (Tanox), (2) factor B inhibitors such as the anti-B antibody TA106 (Taligen Therapeutics), (3) C4 inhibitors (e.g., anti-C4 antibodies) and (4) C1q inhibitors (e.g., anti-C1q antibodies).

Antibodies useful in the present invention, such as antibodies that specifically bind to either C4, C3 or C5 and prevent cleavage, or antibodies that specifically, bind to factor D, factor B, C1q, or the C3a or C5a receptor, can be made by the skilled artisan using methods known in the art. See, for instance, Harlow, et al. (1988, In: Antibodies, A Laboratory Manual, Cold Spring Harbor, N.Y.), Tuszynski et al. (1988, Blood, 72:109-115), U.S. patent publication 2003/0224490, Queen et al. (U.S. Pat. No. 6,180,370), Wright et al., (1992, Critical Rev. in Immunol. 12(3,4):125-168), Gu et al. (1997, Thrombosis and Hematocyst 77(4):755-759) and Burton et al., (1994, Adv. Immunol. 57:191-280). Anti-C3 and anti-C5 antibodies are also commercially available.

The invention encompasses the use of pharmaceutical compositions comprising a complement inhibitor to practice the methods of the invention. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter develop in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, the term "pharmaceutically-acceptable carrier" means a chemical composition with which a complement inhibitor may be combined and which, following the combination, can be used to administer the complement inhibitor to a mammal.

As used herein, the term "physiologically acceptable" ester or salt means an ester or salt form of the active ingredient which is compatible with any other ingredients of the pharmaceutical composition, which is not deleterious to the subject to which the composition is to be administered.

The pharmaceutical compositions useful for practicing the invention are used to treat or contact either the blood or the biomaterial, or both, prior to, during and/or after the extracorporeal treatment. Accordingly, the concentration of active ingredient for such use may range broadly. While the precise dosage administered will vary depending upon any number of factors, including but not limited to, the type of patient, the type or severity of the condition, the age of the patient and the route of administration. Preferably, the dosage of the compound will vary from about 1 mg to about 10 g per kilogram of body weight of the patient. More preferably, the dosage will vary from about 10 mg to about 1 g per kilogram of body weight of the patient. Higher concentrations of active ingredient may be beneficial for application to the biomaterial, as dilution will occur as the blood contacts the biomaterial.

A single complement inhibitor may be administered or applied, or two or more different complement inhibitors may be administered or applied in the practice of the method of the invention. In one embodiment of the invention, the method comprises administration of only a complement inhibitor or a combination of complement inhibitors. In other embodiments, other biologically active agents are administered in addition to the complement inhibitor(s) in the method of the invention. Non-limiting examples of other biologically active agents useful in the invention include anticoagulants anti-thrombotics and anti-inflammatory agents, as would be known and appreciated by the skilled artisan.

As discussed above, the complement inhibitor is used to treat blood just prior to, or during the extracorporeal treatment, or it is used to treat the biomaterial used in the extracorporeal treatment. An alternative or supplementary treatment can involve administering a complement inhibitor to an individual, alone or combined with other anti-coagulants or anti-inflammatory agents before or after the extracorporeal treatment. The sections below address this additional embodiment.

Pharmaceutical compositions that are useful in the aforementioned embodiment may be administered systemically in oral solid formulations, parenteral, intravenous, ophthalmic, suppository, aerosol, topical or other similar formulations. Such pharmaceutical compositions may contain pharmaceutically-acceptable carriers and other ingredients known to enhance and facilitate drug administration. Other formulations, such as nanoparticles, liposomes, resealed erythrocytes, and immunologically based systems may also be used to administer a complement inhibitor according to the methods of the invention.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, in microbubbles for ultrasound-released delivery or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibacterial agents; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The following examples are provided to describe the invention in greater detail. They are intended to illustrate, not to limit, the invention.

EXAMPLE 1

This example describes an investigation into whether hemodialysis biomaterials lead blood leukocytes to express functional TF through complement activation. In particular, it was determined that C5a-C5aR/neutrophils cross-talk plays a role in TF pathway activity in hemodialysis ESRD patients, thereby clarifying a potent mechanism implicated in their thrombotic manifestations.

Materials and Methods:

Study population. Samples from six patients with ESRD on chronic hemodialysis were collected (3 male, age, 62.5±9.16 years, 3 female, age 65.8±5.18 years). All patients are being followed in the Department of Nephrology, University Hospital of Alexandroupolis, Greece. The cause of ESRD was glomerulonephritis in 2 patients, chronic pyelonephritis in 2 patients, diabetes mellitus in one patient, and arterial hypertension in the last subject. Three patients had thrombotic cardiovascular events and two patients had a history of vascular access thrombotic events. Antiplatelet therapy was administered in 3 out of 6 patients, while 3 patients were on low molecular weight heparin. The filters used for hemodialysis were low flux PS in all patients. Additionally, samples from six healthy donors were used in the study.

Isolation of mononuclear and polymorphonuclear cells from peripheral blood. Blood was collected in EDTA-treated tubes (Vacuette, Grenier bio-one, Austria), and PMNs and peripheral blood mononuclear cells (PBMCs) were immediately separated by 1077/1119 Histopaque double-gradient density centrifugation (Histopaque; Sigma-Aldrich) and washed thoroughly in PBS. The absolute number of neutrophils was adjusted to 2—2.4×10$^6$ cells/ml in PBS. Cells were assessed in all experiments for cell purity after cytospin (>98%), viability by trypan blue exclusion (>97%) and platelet contamination (<2 platelets/100 neutrophils). Moreover, May-Grünwald-Giemsa staining did not reveal adhering platelets to neutrophils.

ESRD serum and plasma preparation. Serum samples were drawn from the afferent line immediately before hemodialysis and at specific time points during hemodialysis. All samples were collected in polypropylene tubes without anticoagulant or clot activator. Furthermore, EDTA-treated tubes were used for plasma isolation since they do not interfere with complement activation. Both serum and plasma were isolated after centrifugation at 1.400 g for 15 min at room temperature.

Complement and anaphylatoxin inhibition studies. I) Compstatin, a 13-residue cyclic peptide (Ac-I[CVWQDW-GAHRTC]TNH$_2$) that inhibits the cleavage of native C3 by the C3 convertase, was used as a specific inhibitor of complement activation at the C3 level. In certain studies, a compstatin analog (1-methyl tryptophan as the 4th residue) was used.

A linear inactive analogue of compstatin (IAVWQDW-GAHRTAT-NH$_2$) was used as a control [26]. II) SB-290152, a selective nonpeptide antagonist of the complement anaphylatoxin receptor C3aR, was used in this study to dissect the involvement of C3aR signalling in the generation of neutrophil derived TF [27]. III) To block C5aR stimulation on neutrophils, a small cyclic hexapeptide (AcF-[OPdChaWR]) that acts as a selective C5aR antagonist [28, 29] was used. Sera were pre-incubated for 30 min with Compstatin or its linear analogue (15 µM final concentration), before incubation with leukocytes. Furthermore, serum for stimulation was added to leukocytes that had been pre-incubated for 30 min with C3aRa or C5aRa (5-10 µM final concentration). Approximately 0.8-110$^6$ washed cells from healthy donors were used for the subsequent incubations, The final volume was adjusted with PBS at 250 µl and the leukocytes were incubated for 90-120 min at 37° C. The effects of complement antagonists were found to be dose-dependent, reaching peak activity at the doses chosen for this study.

Modified prothrombin time (mPT) assay to examine TF mediated coagulation activity in cell supernatants, complement inhibition and anaphylatoxin receptor studies. Since it has been shown previously that TF dependent procoagulant activity in leukocyte culture supernatants is altered after C5a/C5aR stimulation or blockade [30], the mPT method was used in order to estimate primarily the kinetics of TF induction. The presence of TF in supernatants is probably due to the presence of the soluble, spliced TF isoform [31] or TF microparticles.

At the end of the incubation period, supernatants of cells were collected by centrifugation at 800 g for 10 min and were checked a second time to confirm the absence of cells and platelets. The coagulation activity properties (TF/FVIIa binding activity) of the cell supernatants were determined using a modified prothrombin time (mPT) assay. Briefly, after performing the "classic" PT test (100 µl platelet poor plasma [PPP] plus 200 µl thromboplastin ISI 1.7 (Instrumentation Laboratory, Milan, Italy), the modified PT analysis was carried out. Namely, 125 µl of cell supernatant and 75 µl thromboplastin were added to 100 µl of PPP to measure the changes of PT. As control of mPT, 125 µl of PBS was used instead of cell supernatant and the in vitro clotting time usually ranged from 31 to 34 sec.

To verify that the thromboplastic activity was due to TF alone, supernatants were incubated for 30 min with a specific neutralizing anti-TF monoclonal antibody (mAb, No 4509, American Diagnostica, Greenwich, Conn., USA), 10 µg/ml, at room temperature. PT was then measured by the mPT method. Non-specific controls involved incubation with the same subclass and concentration of mouse anti-human antibodies, as well as with different secondary antibodies.

RNA extraction, RT & relative quantitative real-time PCR analysis. Total RNA was isolated from double-gradient purified peripheral blood PMNs and PBMCs using the TRIzol reagent (Invitrogen, Carlsbad, Calif., USA) according to manufacturer's instructions. cDNA was synthesized from 1 µg of isolated RNA using Superscript III reverse transcriptase (Invitrogen, Carlsbad, Calif., USA). In order to quantify the relative expression level of the two TF isoforms with coagulant properties [(full-length TF (referred to hereafter as 'TF') and alternative spliced TF (asTF)], isoform specific real-time PCR was performed. In each sample TF, asTF and GAPDH mRNA sequence-specific primers and probes for detection were applied. The $2^{-DDCT}$ method was used for quantification of the target gene expression.

Western blot analysis. Approximately 110$^6$ cells were resuspended in lysis buffer, containing 1% Triton-X in 150 mM NaCl, 20 mM HEPES (pH 7.5) with protease inhibitors (Complete Protease Inhibitor Tablets, Roche). After freezing and thawing for a minimum of three times, lysates were centrifuged and supernatants were quantified using the BCA Protein Assay (Pierce). Proteins (70 µg of protein per lane) were diluted 1/1 in 2×SDS loading buffer, heated at 100° C. for 5 min and analyzed in a 10% Criterion pre-cast SDS PAGE gel (BioRad, CA). Subsequently, membranes were electroblotted onto methanol treated PVDF membranes (Bio-Rad, CA) and blocked in 5% non-fat dry milk in TBS containing 0.1% Tween 20 (TBS-T) for 1 h at RT. Membranes were incubated with anti-TF polyclonal antibody (4501, American Diagnostica Inc, Stamford, Conn.) for 3 h or with G3PDH polyclonal antibody (2275, R&D Systems Inc.), in order to confirm equal loading, 2 h at RT in dilutions of 1/1000 and 1/5000, respectively. Membranes were washed thoroughly with TBS-T and incubated with Horseradish peroxidase (HRP)-linked whole anti-goat (HAF109, R&D Systems Inc) and anti-rabbit antibodies (HAF008, R&D Systems Inc) in a dilution of 1:2000 and 1:10000 respectively for 1.5 h at RT. After a wash in TBS-T, immunoreactive proteins were detected using enhanced chemiluminescence (ECL) detection system (Western Blotting Luminol sc-2048, Santa Cruz Biotechnology) and visualized by exposure on X-ray film (Agfa medical x-ray film, Agfa-Gevaert, Belgium).

Flow cytometry analysis of peripheral blood leukocytes. Indirect intracellular FITC labelling was carried out in PMNs. This protocol was followed, since it provided more efficient staining than using FITC conjugated TF monoclonal antibodies. Cells were identified by their forward and side scatter characteristics and specific cell surface markers (CD14). Median Fluorescence Intensity (MFI) ratio was applied.

Statistical analysis. Associations were considered to be statistically significant if the p value was <0.05. Data are presented as mean±standard deviation (M$^±$SD) and were processed using the Student's t-test and Mann-Whitney non-parametric (paired) test for paired means, to compare differences in means. The Mann-Whitney non-parametric test was performed when the sample number was limited (n<10). The analysis was conducted with GraphPad Prism software (Version 4.03, GraphPad Software Inc).

It is noted that contamination of all materials not tested by their respective manufacturers was excluded using the *Limulus* amebocyte assay (Sigma-Aldrich).

Results:

Serum of ESRD patients exerts procoagulant activity through TF induction and follows a time dependent manner during the hemodialysis course. To evaluate whether ESRD serum induces procoagulant activity, peripheral blood PMNs and mononuclear cells from healthy volunteers (N=4) were separately incubated with 50 µl of serum (⅕ of final volume) from 6 ESRD patients collected during several time points of hemodialysis (immediately before hemodialysis and after 1 min, 15 min, 30 min, 60 min, 120 min, and 240 min). Moreover, supernatants obtained after incubation of healthy blood leukocytes with serum from healthy subjects were used as negative controls since their serum does not exhibit procoagulant activity, while supernatants from cells incubated with APS serum were used as positive controls. The procoagulant activity of the above cell culture supernatants was measured using the mPT method.

The mean "classic" PT was 12.76$^±$0.17 sec at baseline, while the mean baseline modified PT (mPT) was 33.34$^±$0.96 sec. The supernatants from unstimulated neutrophils as well as from cells incubated with sera of healthy subjects did not show any procoagulant activity (FIG. 1A—bar 1: 33.27±0.60 sec and bar 2: 32.07±0.09 sec, respectively; p=n.s.—non significant—compared to baseline mPT). Supernatants of neutrophils incubated with sera of ESRD patients before hemodialysis (predialysis status) exhibited a weak procoagulant activity (FIG. 1A—bar 3: 29.07±0.33 sec, p<0.05 compared to bars 1, 2), suggesting that these patients might be at increased procoagulant risk. Supernatants of cells incubated with serum taken after the first minute of hemodialysis exhibited potent procoagulant properties, as the mPT was markedly decreased to 25.59±0.43 sec (FIG. 1A—bar 4 p<0.001 compared to predialysis and controls). The above finding supports the hypothesis that the biomaterial-induced procoagulant effects represent an acute phenomenon of immediate induction. The procoagulant activity remained significant during the first 30 minutes of hemodialysis and was gradually abolished after the first hour, based on mPT values that were 23.44±0.51 sec at 15 min (FIG. 1A—bar 5 p<0.001 compared to predialysis), 24.2±0.39 sec at 30 minutes (bar 6 p<0.001 compared to predialysis), 26.21±0.04 sec at 60 min (bar 7: p=n.s. compared to predialysis), 28.35±0.41 sec at 120 min (bar 8 p=n.s. compared to predialysis), and 29.32±0.17 sec at 240 min (bar 9: p=n.s. compared to predialysis). Supernatants of neutrophils incubated with APS serum showed marked procoagulant activity (FIG. 1A—bar 10: 20.39±0.55 sec, p<0.001 compared to bars 1, 2).

To determine if the observed procoagulant activity was TF dependent, a highly specific anti-TF mAb was added to the supernatants showing the procoagulant effects at a dilution of 1/100. It was observed that the procoagulant activity was completely abolished (FIG. 1A—bar 11: 32.81±0.48 sec p<0.001 compared to all values during hemodialysis and ESRD serum before hemodialysis) reaching the values of healthy individuals (FIG. 1A—bars 1, 2), reversing even the predialysis TF activity (FIG. 1A—bar 3). The addition of other monoclonal or polyclonal antibodies at various concentrations did not affect the mPT values, indicating that the procoagulant properties of ESRD serum during hemodialysis are entirely TF-dependent. This underscores the central role of TF in the ESRD prothrombotic activity. Additionally, neither the reagents used in the experimental setting nor the ESRD serum alone had any effect on mPT values. Moreover, the anti-TF mAb at both low and high concentration dilutions (1/100, 1/50, 1/5 w/v) was not able to inactivate the exogenous thromboplastin and had no effect on baseline mPT levels.

Similar functional procoagulant activity pattern was also observed in supernatants of PBMCs cultures following the same stimulation protocol as in PMNs (FIG. 1B).

The data provided from the above functional assay were confirmed performing rt RT-PCR in RNA isolated from the cultured PMNs and PBMCs at three selected representative time points (predialysis, 30 min, 120 min). The mRNA expression pattern of TF was consistent with the observed procoagulant activity. More specifically, the data acquired from six independent experiments showed that predialysis serum induced a 1.72 fold increase of TF expression in healthy PMNs (average DCt 8.44±0.25 compared to unstimulated; 9.22±0.33, p<0.01), whereas serum isolated 30 min after the beginning of hemodialysis caused a significant elevation of TF expression (2.53 fold increase, average DCt 7.88±0.39 compared to 9.22±0.33, p<0.01). TF mRNA expression of the incubated PMNs with sera at 120 min was decreased (2.22 fold increase average DCt 8.07±0.28 compared to 9.22±0.33, p<0.01).

Blood leukocytes on hemodialysis treatment of ESRD patients express TF in a similar pattern to their serum procoagulant properties. The previous findings indicating that ESRD serum has the ability to induce TF expression from healthy blood leukocytes prompted an investigation into whether blood leukocytes from ESRD patients are able to express TF in vivo.

Given that neutrophils are strongly activated during the hemodialysis course, thus playing a crucial role in different related disorders [35-37], and knowing that these cells contribute to functional TF expression under certain stimuli [24, 30, 33, 38], this population was analyzed first at the RNA level. Peripheral blood PMNs from 6 ESRD patients were isolated at predialysis status and two selected time points of the hemodialysis procedure (showing different serum procoagulant activity; 30 and 120 min). Real time RT-PCR revealed an overexpression of both TF isoforms (FIG. 2A—I) in a pattern similar to that of their serum mPT procoagulant activity. Subsequently, TF expression levels were examined at protein level. Flow cytometry analysis for PMNs was performed and the MFI values revealed a pre-existing TF protein expression at predialysis status (FIG. 2B I—predialysis; bar 2: 1.66±0.16 vs. healthy controls; bar 1, p<0.05) displaying a peak expression at the same time point as shown in rt RT-PCR (FIG. 2B I—30 min; bar 3: 2.16±0.06 vs. bar 1, p<0.05). TF protein overexpression was also observed after Western blot analysis (FIG. 2C).

Figure 2:
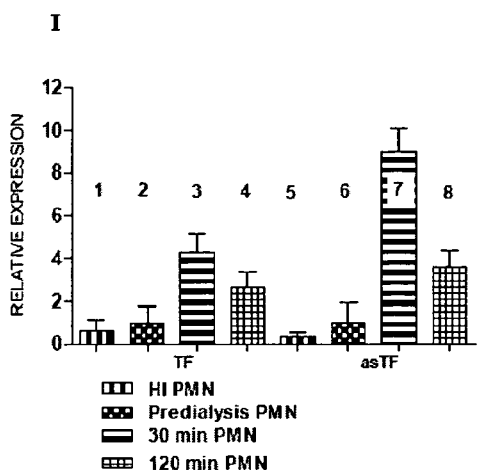
FIG. 2: TF expression in ESRD peripheral leukocytes at both mRNA and protein levels. A: Relative quantification of TF and asTF in ESRD patient leukocytes (N=6) using real time RT-PCR. $2^{-DDCT}$ analysis indicated that tissue factor mRNA in PMN (I) and PBMC (II) population was over expressed at the first 30 min of hemodialysis (average DCt values±SD; bar 3: 8.6±0.88 and 7.33±0.28 vs. bar 2: 10.7±0.79 and 8.86±0.66 respectively, $p<0.01$), while at 120 min mRNA expression was reduced (bar 4: 9.28±0.72 and 7.9±0.41 vs. bar 2, respectively, $p<0.05$). Similar results were observed in asTF mRNA expression (average DCt values; bar 7: 11.331±1.1 and 13.03±0.3 vs. bar 6: 14.5±0.93 and 13.88±0.22, respectively, $p<0.05$ and bar 8: 12.66±0.82 and 13.5±0.18 vs. bar 6, $p<0.05$). B: Isolated PMNs (I) and PBMCs (II) from ESRD patients (N=6) at predialysis and at two representative time points of hemodialysis (30 and 120 min) were intracellularly stained with anti-TF. MFI in fold expression revealed a peak TF expression at the first 30 min (bar 3) and was reversed at 120 min (bar 4). It is noteworthy that TF appears to be elevated even at predialysis status (bar 2) compared to healthy control (HI: bar 1). On the FITC graph, PMN isotype control is shown as shaded gray, and the remaining peaks from left to right are: PMN HI, PMN ESRD 120 min, PMN ESRD predialysis and PMN ESRD 30 min. C: Western blot analysis (representative data from 4 experiments) detected a pattern of TF expression similar to that of the flow cytometry data (lysates from neutrophils incubated with serum at predialysis status (ii), taken at 30 (iii) and 120 min (iv) of hemodialysis). Lysates from blood cells incubated with PBS were used as a negative control (i).
Figure 2:
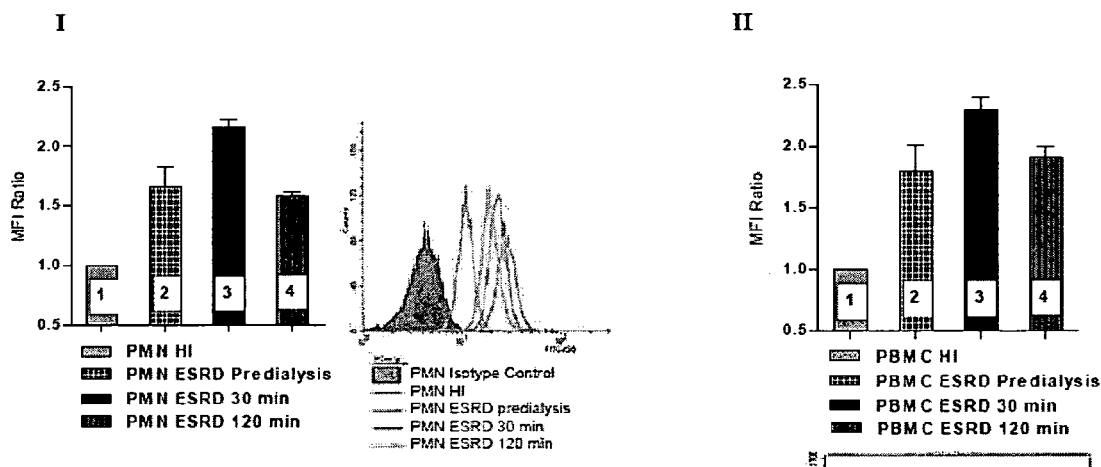
Figure 2:
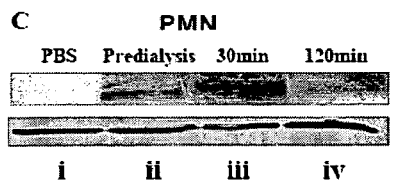

Finally, the PBMC population showed similar TF expression at mRNA levels to that of PMNs (FIG. 2A II), whereas FACS analysis indicated that the main source of TF in PBMCs are the CD14 positive cells (FIG. 2B II: predialysis; bar 2: 1.8±0.21 vs. healthy controls bar 1, p<0.05 and 30 min bar 3: 2.3±0.1 vs. bar 1, p<0.05). Western blot analysis data were similar to those for PMN population. These findings indicate a time dependent manner of activation of the extrinsic coagulation system during the hemodialysis course, via inflammatory cells such as PMNs and monocytes, in ESRD patients.

Figure 3:
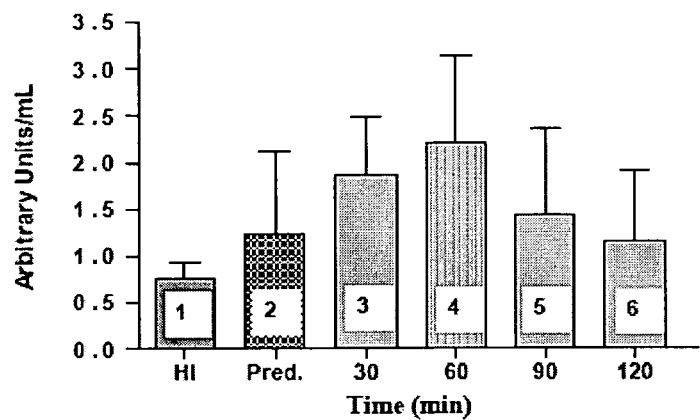
FIG. 3: Complement activation in hemodialysis ESRD plasma. TCC levels in plasma collected from ESRD patients at different time points of hemodialysis were measured using ELISA. TCC increased during the hemodialysis procedure; bar 2, 3, 4. These data were in concordance with the procoagulant activity differences observed in ESRD patients sera over the same time course.
Figure 3:
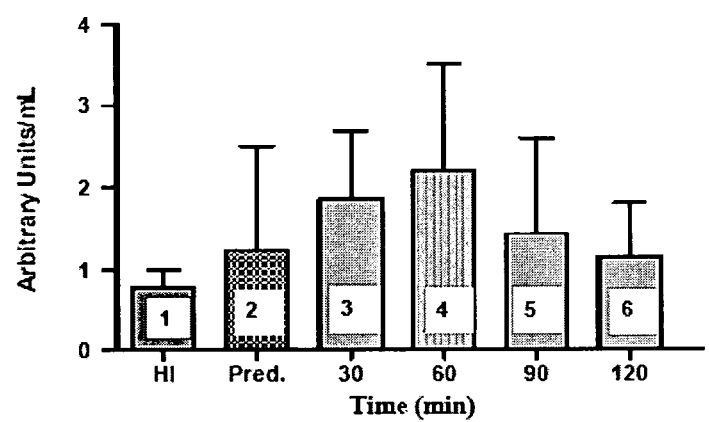

Complement is activated during hemodialysis course in ESRD patients. Given that hemodialysis biomaterials induce complement activation and considering the previously observed complement-leukocyte crosstalk with subsequent TF expression [24, 30], a time point analysis of complement activation during the hemodialysis procedure was conducted. Plasma from four ESRD patients at predialysis status and at several time points of hemodialysis was isolated and used to determine complement activation. TCC levels at predialysis status were slightly elevated (FIG. 3—bar 2) compared to healthy controls (FIG. 3—bar 1), but at less than statistical significance. Plasma samples taken within the first hour of hemodialysis denoted elevated levels of TCC (FIG. 3—bars 3, 4), while the values of the complex were decreased at samples that were isolated after the first hour of hemodialysis procedure (FIG. 3—bars 5, 6). The pattern of complement activation during the course of hemodialysis showed resembled the variations of procoagulant activity caused by the ESRD sera as shown in FIG. 1, probably underlining a link between complement and the coagulation cascade in ESRD patients' blood leukocytes.

TF dependent procoagulant activity in ESRD patients is C5a mediated and dialyzer fibers trigger the extrinsic coagulation system through C5a signaling. The above findings collectively indicated a homologous "bell shaped" time dependent pattern in both TF expression and complement activation during the hemodialysis course. This, coupled with another study [24], showing that complement activation is essential for leukocyte-derived TF, prompted the performance of complement inhibition studies in order to investigate whether hemodialysis biomaterials are potent TF inducers via complement activation.

Figure 4:
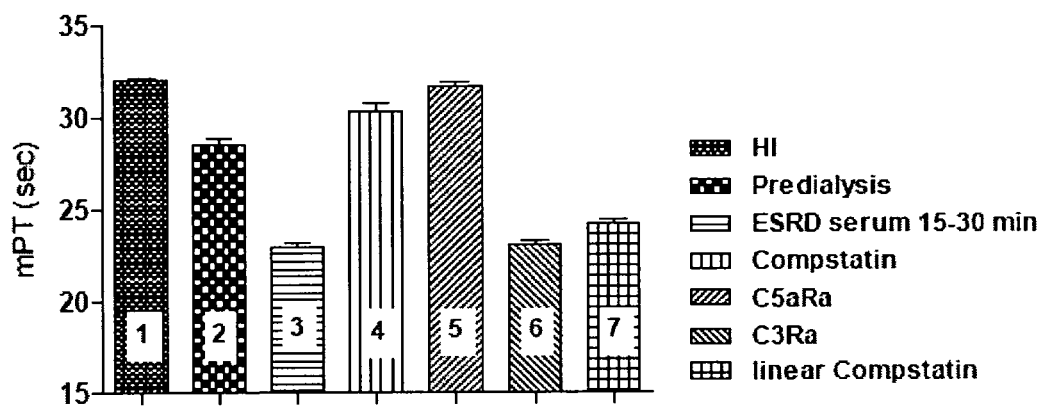
Figure 4:
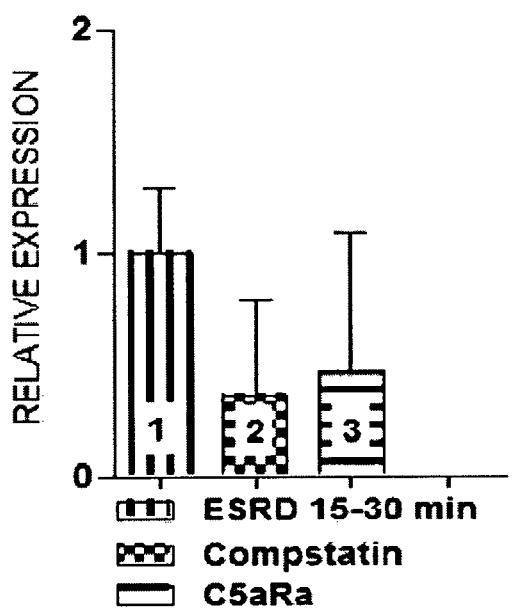

A first set of experiments was performed to determine if the TF procoagulant properties of ESRD serum are complement mediated. Since biomaterial-induced complement activation occurs primarily via both the classical and alternative pathways, compstatin was used to inhibit complement activation at C3 level. It was found that the procoagulant properties of the pretreated sera were significantly reduced (FIG. 4A—bar 4) upon compstatin treatment, reaching the control's mPT values (FIG. 4A—bar 1).

Complement anaphylatoxin inhibition studies followed, as it has been established that hemodialysis biomaterial-induced complement activation results in the production of C3a and C5a. Furthermore, C5aRs seem to mediate TF-dependent thrombotic mechanisms in animals [39, 40] and humans [24]. These experimental data depicted that the addition of C5aR antagonist abrogated the observed procoagulant activity (FIG. 4A—bar 5), whereas preincubation of cells with C3aRa did not affect the mPT values (FIG. 4A—bar 6), suggesting that TF induction is not mediated by C3aRs.

The functional experiments were also confirmed at the RNA level. The $2^{-DDCT}$ analysis of TF expression in PMNs showed that use of compstatin (FIG. 4B—bar 2) and C5aR antagonist (FIG. 4B—bar 3) inhibited the stimulation effect. Similar TF activity and expression pattern after complement inhibition studies was observed in PBMC population.

All of the above-described findings indicate that complement activation induced by hemodialysis biomaterials precedes leukocyte-derived TF activity, underlining the tight and complex interplay between complement, circulating blood cells and coagulation.

In a second set of experiments, it was further shown in vitro that dialyzer fibers are responsible for the complement activation, with subsequent TF expression both in healthy individuals and ESRD patients, thus confirming the crucial role of biomaterials in the previous ex vivo and in vivo findings. As shown in FIG. 5A, compstatin was able to inhibit complement activation induced by hemodialysis biomaterials over time, at two different concentrations. By comparison, complement activation was not inhibited by an inactive linear analog of compstatin.

After incubation of healthy serum with hollow filter fibers (50 mg/ml) a time-dependent procoagulant activity in neutrophil culture supernatants was observed (FIG. 5B bars 2-5). This activity was completely attenuated after addition of anti-TF mAb (FIG. 5B—bar 6). The TF activity was due to complement activation since Compstatin or C5aR antagonist caused elevation in the mPT values (FIG. 5C—bars 4, 7 and bars 5, 8, respectively). C3aR antagonism had no effect on the procoagulant activity.

Complement involvement (FIG. 6A—bar 3: 1.01±0.01, p<0.05 vs. bar 2 and FIG. 6B—III) of the biomaterial induced TF antigen expression (FIG. 6A—bar 2: 1.24±0.02, p<0.05 vs. bar 1 and FIG. 6B—IV) was also confirmed at protein level. The in vitro experimental set was also conducted in PBMCs and the data obtained were similar to those of PMNs.

Discussion:

The studies described above establish that serum from ESRD patients during hemodialysis exerts TF associated procoagulant activity in a time dependent manner, reaching in a peak activity during the $15^{th}$-$30^{th}$ min of hemodialysis, Patients' serum functions in vitro as an agonist to healthy blood leukocytes, leading to TF expression. This in vitro ability was also consistent with in vivo measurements, indicating that ESRD patients' leukocytes express TF during hemodialysis in a similar time dependent manner as was observed in the in vitro experiments, thus suggesting that patients' blood leukocytes constitute a source of blood-borne TF. It was also confirmed that ESRD plasma demonstrated complement activation and that TF-dependent leukocyte procoagulant activity requires complement activation, since it appeared to be completely attenuated by complement inhibition. Anaphylatoxin C5a has been pointed as the main culprit for this in vitro TF induction by leukocytes, thus indicating an interface between inflammation and thrombosis in this clinical entity. Finally, biomaterial fibers have been found in vitro to be able to activate the complement in serum originating from both healthy donors and ESRD patients, thus leading, through C5a to the subsequent TF induction from blood leukocytes.

Thrombotic complications in hemodialysis ESRD patients represent a common and significant clinical problem. Biomaterial-induced effects on inflammation and coagulation have recently attracted wide scientific interest [18, 19]. However, clear causal mechanisms resulting in thrombotic events have not been described in these patients. Hemodialysis procedure is considered a strong inducer of inflammatory mechanisms [43]. Among various inflammatory mediators and cells involved during hemodialysis therapy, complement activation [44] and neutrophil stimulation [45-47] largely contribute in clinical manifestations of this disorder. However, a direct link between them and ESRD thrombogenicity has never been indicated.

Studies in both humans and animal models indicated that TF expression by leukocytes plays an important role in thrombosis associated with a variety of diseases [48]. Moreover, recent findings have established an interface between inflammation and coagulation through C5a and leukocyte C5a receptor cross-talk, thus leading to TF induction [30, 40]. Although it known that activated CD14 monocytes are able to produce TF; the inventors considered it important to investigate a possible thrombogenic role of neutrophils in this disorder. Neutrophils, as a major blood population that becomes highly activated and accumulated by hemodialysis biomaterials [49], provoked the inventors to clarify if they represent a potent partner that bridges inflammation and thrombosis in this clinical model. Given that complement is activated in the course of hemodialysis [15, 16] and that neutrophils are highly activated [17], the inventors hypothesized that these cells among blood leukocytes would express TF as a result of their activation by C5a. Although TF represents the basic initiator of coagulation in vivo and holds a central role in the thrombotic process [48, 50], data regarding its role in ESRD-related thrombosis are surprisingly limited [51-57]. More recently, an increased activity of TF pathway was shown in patients on dialysis, but a pathophysiologic mechanism linking inflammation and coagulation refining the stimulus and the source of the increased TF in this disorder was absent [58]. Thus, without intending to be limited by any explanation of mechanism, the findings presented herein suggest a mechanism involving the complement activation on patient serum with subsequent induction of neutrophils and CD14+ cells through C5a/C5aR which once stimulated express functional TF. Moreover, the observations indicating the ability of ESRD serum to induce via C5a, TF expression by healthy PBMCs and PMNs, were not only restricted in vitro experiments but were also supported by in vivo analyses indicating that ESRD patient leukocytes, during hemodialysis course, expressed TF in a similar time pattern as was observed in the in vitro experiments.

The mechanisms of biomaterial-induced thrombus formation are not completely elucidated [58]. The present study suggests a potential mechanism of hemodialysis biomaterials to induce procoagulant properties via complement activation. These findings bridge the biomaterial-induced inflammation and the ESRD thrombogenicity, indicating that the TF expression by neutrophils and monocytes, via C5a/C5a receptors cross-talk, was dependent on the contact of serum (healthy or patient) with fibers, indicating thus that the dialyzer fibers act as a culprit for this complement activation with subsequent TF expression. This in vitro experimental set mimics only the role of fibers, due to the difficulty in applying an extracorporeal circuit model in order to simulate the hemodialysis procedure, checking thus hemodialysis materials other than filters. However, the use of cuprophane filters, instead of those made by polysulfone in the above-described in vitro experiments revealed similar pattern of C5a dependent TF activity.

According to the findings set forth above, the TF procoagulant properties of ESRD serum reach a peak at 15 to 30 min after hemodialysis and gradually decrease thereafter. These results clearly suggest that biomaterials used in hemodialysis induce complement activation acutely (even from the first minute of hemodialysis). Furthermore, an increase of TCC was observed, reaching a peak one hour after the hemodialysis stimulation. Bridging the time-dependent coagulant properties and complement-activation findings to previous studies, different hypotheses can be formulated. For instance, and again without intending to limit the invention, it may be that adherent leukocytes on the hemodialysis filter undergo activation, thereby releasing various molecules negatively regulating complement components, thus leading to such complement-dependent kinetics of TF expression as those observed in the foregoing experiments. The potential involvement of stimulated leukocytes in mechanisms related to complement regulation could be also supported by previous findings indicating that reused dialyzers cause attenuation of complement activation, and also by the above experiments showing that the contact of serum with fibers in the absence of cells constantly induces complement activation. In addition, previous in vitro data [61] indicated that neutrophils returning to the circulation after hemodialysis induced pulmonary leukostasis are unable to react to the $C5a_{desarg}$. This may be linked to the aforementioned in vivo findings showing lower leukocyte TF expression levels after one hour, despite the higher TCC levels observed in this time point. Based on recent studies, an additional mechanism of this phenomenon could be the internalization of C5a receptors as a response to the constant presence of C5a ligand [61], leading to attenuation of TF induction, similarly to what was observed after C5aR specific antagonism.

Thus, in appears that, in patients on hemodialysis, their neutrophils and monocytes may have more than one role. First, they are rapidly triggered for TF expression via C5a generation. A later role of leucocytes is disclosed 60-90 min after the course and possibly related to their protective activity via the release of complement inhibitors or by acquiring complement "resistance" during their pulmonary stasis or internalization of C5a receptors, thus offering patients an "umbrella" from a long term complement activity with subsequent TF over-expression. Furthermore, the previously described progressive increase of TFPI during the extracorporeal circuit [54-58] may constitute a complementary protective mechanism against dialysis TF "overdose," thus suggesting an additional effort to prevent this complement-dependent triggering of TF pathway.

The chronic inflammation in hemodialysis ESRD patients results in a basal prothrombotic state, as shown by the reduced mPT (caused by predialysis patient serum compared to serum of healthy controls) and TF mRNA and protein expression studies on leukocytes. The observed complete attenuation of coagulation activity by the specific monoclonal anti-TF antibody suggests that the predialysis prothrombotic tendency of ESRD patients is also TF-dependent. In addition, the use of Compstatin and C5aR antagonist indicates that complement activation induced by pulsed chronic contact to biomaterials might, at least in part, be an effector of the prothrombotic state of such patients.

TF expression through biomaterial C5a/C5aR activation, ranks the ESRD clinical model in a wider group of acquired thrombotic disorders induced by this cross-talk, such as APS [24], sepsis [63-65] and ARDS [30], thus indicating that the close interaction of complement and thrombosis might be a more universal phenomenon. Current therapeutic strategies have reduced the incidence of thrombotic events; however, the results achieved are far from optimal. The findings set forth herein, indicating biomaterial-induced procoagulant activity mediated by a chain of subsequent "domino" events, including complement activation, C5a production, neutrophils and other cells (e.g. CD14 monocytes) C5aR stimulation and finally TF generation, provide important evidence on a novel thrombotic process that is largely unaffected by treatment strategies applied to patients with ESRD. This observation points to potential therapeutic targets of significance. The development of biomaterials devoid of inducing complement activation, complement inhibition by compstatin or similar analogues, C5aR blockade by specific inhibitors and the application of selective TF inhibitors or use of TFPI are expected to be beneficial in patients with ESRD and result in reduction of thrombotic complications in such patients.

EXAMPLE 2

This example sets forth experimental evidence showing that hemodialysis-induced complement activation and subsequent TF upregulation in peripheral blood leukocytes can be efficiently reduced by inhibiting complement activation. A protocol was devised to mimic hemodialysis procedure. Whole blood obtained from healthy donors was circulated in a hemodialysis machine, which is normally used to perform this procedure in adult patients.

Materials and Methods:

Whole blood was collected from healthy volunteers. Lepirudin (Refludan) was used as anticoagulant (50 ug/ml), since it does not interfere with the complement pathway. All experiments were started within 30 min after blood collection.

To minimize the blood volume needed, HPH Junior polysulfone dialyzers (Minntech Corporation) were used. Standard bloodline components served as tubing system (Arterial & venous blood lines, Set a/v for Fresenius 2008/4008, HMC Premedical S.p.A., Italy). In each experiment, two circuits (in the presence of 40 uM of a compstatin analog or an inactive control peptide, respectively) were evaluated in parallel. The compstatin analog (sometimes referred to as "compstatin 4[1MeW]") was I[CV$^{(1-Me)}$WQDWGAHRC]I—NH$_2$ (SEQ ID NO:4). The inactive control peptide was I[C$^{(N-Me)}$G$^{(1-Me)}$WQDWGAHRC]I—NH$_2$ (SEQ ID NO:5).

To prevent any ultrafiltration, the dialysate compartment was filled with saline solution (0.9% NaCl) and clamped. The circuits were pre-rinsed with saline solution for approximately 30 minutes. The saline solution was then removed and the circuits were filled with blood. Blood volume was adjusted to 35 ml in each circuit and flow rate at 200 ml/min, 37° C.

Blood samples were taken at several time points: 0 min (pre-dialysis), 2 min, 15 min, 30 min, 60 min, 90 min and 120 min from the two circuits using syringes prefilled with EDTA to prevent further complement activation.

To examine the activation of crucial pathways involved in the interaction of blood with the artificial surface of the dialyzer, complement, coagulation and neutrophil activation were analyzed. Briefly, complement activation was measured in plasma using a monoclonal antibody C3-9 (2 ug/ml), which recognizes a neoantigen that is exposed in C3($H_2O$), C3b and C3c but not in native C3. Neutrophil activation was assessed using flow cytometry after surface staining of CD11b (PE Mouse Anti-human CD11b/Mac-1, Cat. No 555388, BD Pharmigen). Tissue factor (TF) protein expression was used as a marker of coagulation pathway activation. TF expression was examined in purified neutrophils after intracellular indirect staining (MAb ag. human tissue factor, Cat. No 4509, American Diagnostica and FITC goat Anti-mouse IgG/IgM.

Results:

Passing whole blood through the hemodialysis circuit induced time-dependent complement activation, as demonstrated by an increase in amounts of C3 cleavage products in plasma, which was proportional to the duration of the blood contact with the elements of this circuit (FIG. 7A). The addition of 40 uM of compstatin analog 4[1MeW] abrogated this activation.

Cellular and coagulation cascade activation were analyzed in blood neutrophils after surface staining for CD11b and intracellular staining for TF, using flow cytometry. Cellular and coagulation cascade activation were upregulated during the hemodialysis simulation (FIG. 7B, FIG. 7C. Treatment with compstatin analog 4[1MeW] attenuated both types of complement activation (FIG. 7B, FIG. 7C).

References:
1. Sarnak M J, Levey A S, Schoolwerth A C et al. Kidney disease as a risk factor for development of cardiovascular disease. A statement from the American Heart Association Councils on Kidney in Cardiovascular Disease, High Blood Pressure Research, Clinical Cardiology, and Epidemiology and Prevention. Hypertension. 2003; 42: 1050-1065.
2. US Renal Data System. Causes of death in ESRD. Am J Kidney Dis 1999; 34 (suppl 1): S87-S94.
3. US Renal Data System. USRDS 2001 annual data report: atlas of end-stage renal disease in the United States. Bethesda (MD): National Institutes of Health, National Institute of Diabetes and Digestive and Kidney Diseases; 2001.
4. Culleton B F, Larson M G, Wilson P W F et al. Cardiovascular disease and mortality in a community-based cohort with renal insufficiency. Kidney Int 1999; 56: 2214-2219.
5. Sarnak M J, Levey A S: Epidemiology of cardiac disease in dialysis patients. Semin Dial 1999; 12: 69-76.
6. Jungers P, Khoa T N, Massy Z A et al. Incidence of atherosclerotic arterial occlusive accidents in predialysis and dialysis patients: a multicentric study in the Ile de France district. Nephrol Dial Transplant 1999; 14: 898-902.
7. Culleton B F, Wilson P W. Cardiovascular disease: risk factors, secular trends, and therapeutic guidelines. J Am Sac Nephrol 1998; 9: S5-15
8. Collins A J. Cardiovascular mortality in end-stage renal disease. Am J Med Sci 2003; 325(4): 163-167.
9. Rosamond W D, Chambless L E, Folsom A R et al. Trends in the incidence of myocardial infarction and in mortality due to coronary heart disease. N Engl J Med 1998; 339: 861-867
10. Appel L J. Beyond (or back to) traditional risk factors: preventing cardiovascular disease in patients with chronic kidney disease. Ann Intern Med 2004; 140: 60-61.
11. Foley R N. cardiac disease in chronic uremia: can it explain the reverse epidemiology of hypertension and survival in dialysis patients? Seminars in dialysis 2004; 17(4): 275-278.
12. Lowrie E G, Lew N L: Death risk in hemodialysis patients: The predictive value of commonly measured variables and an evaluation of death rate differences between facilities. Am J Kidney Dis 1990; 15: 458-482.
13. Yeun J Y, Levine R A, Mantadilok V et al: C-reactive protein predicts all cause and cardiovascular mortality in hemodialysis patients. Am J Kidney Dis 2000; 35: 469-476.
14. Stenvinkel P, Carrero J J, Axelsson J et al: Emerging biomarkers for evaluating cardiovascular risk in the chronic kidney disease patient: How do new pieces fit into the uremic puzzle? Clin J Am Soc Nephrol 2008; 3: 505-521.
15. Chenoweth D E. Complement activation during hemodialysis: clinical observations, proposed mechanisms, and theoretical implications. Artif Organs 1984; 9: 281-90.
16. Agostini A, Gardinali M. Complement activation during hemodialysis. J Biomater Appl 1989; 4: 102-22.
17. Nilsson B, Larsson R, Hong J et al. Compstatin inhibits complement and cellular activation in whole blood in two models of extracorporeal circulation. Blood 1998; 92: 1661-1667.
18. Nilsson B, Ekdahl K N, Mollnes T et al. The role of complement in biomaterial-induced inflammation. Mol Immunol 2007; 44: 82-94.
19. Gorbet M B, Sefton M V, Biomaterials-associated thrombosis: roles of coagulation factors, complement, platelets and leykocytes. Biomaterials 2004; 25: 5681-5703.
20. Gasque P. Complement: a unique innate immune sensor for danger signals. Mol. Immunol. 2004; 41: 1089-1098.
21. Kaysen G A. The microinflamxnatory state in uremia: causes and potential consequences. J Am Soc Nephrol 2001; 12: 1549-1557.
22. Zimmermann J, Herrlinger S, Pruy A et al. Inflammation enhances cardiovascular risk and mortality in hemodialysis patients. Kidney Int. 1999; 55: 648-658.
23. Schenone M, Furie B C Furie B. The blood coagulation cascade. Curr Opin Hematol 2004; 11: 272-277.
24. Ritis K, Doumas M, Mastellos D et al. A Novel C5a Receptor-Tissue Factor Cross-Talk in Neutrophils Links Innate Immunity to Coagulation Pathways. J Immunol 2006; 177: 4794-4802.
25. Mallik B, Katragadda M, Spruce L A et al. Design and NMR characterization of active analogs of compstatin containing non-natural amino acids. J Med Chem 2005; 48: 274-286.
26. Sahu A, Kay B K, Lambris J D. Inhibition of human complement by a C3-binding peptide isolated from a phage-displayed random peptide library. J Immunol 1996; 157: 884-891.
27. Ames R S, Lee D, Foley J J et al. Identification of a selective nonpeptide antagonist of the anaphylatoxin C3a receptor that demonstrates anti-inflammatory activity in animal models. J Immunol 2001; 166: 6341-6348.
28. Mastellos D, Papadimitriou J C, Franchini S et al. A novel role of complement: mice deficient in the fifth component of complement (C5) exhibit impaired liver regeneration. J Immunol 2001; 166: 2479-2486.
29. Lappegard K T, Riesenfeld J, Brekke O L et al. Differential effect of heparin coating and complement inhibition on artificial surface-induced eicosanoid production. Ann Thorac Surg 2005; 79: 917-923.
30. Kambas K, Markiewski M M, Pneumatikos I A et al. C5a and TNF-alpha up-regulate the expression of tissue factor in intra-alveolar neutrophils of patients with the acute respiratory distress syndrome. *J Immunol* 2008; 180 (11): 7368-75.

31. Szotowski B, Antoniak S, Poller W et al. Procoagulant soluble tissue factor is released from endothelial cells in response to inflammatory cytokines. *Circ Res* 2005; 96: 1233-1239.)

32. Livak K J, Schmittgen T D. Analysis of relative gene expression data using real time quantitative PCR and the $2^{-DDCT}$ method. *Methods* 2001; 25: 402-408.

33. Rafail S, Ritis K, Schaefer K et al. Leptin induces the expression of functional tissue factor in human neutrophils and peripheral blood mononuclear cells through JAK2-dependent mechanisms and TNFalpha involvement. *Thromb Res* 2008; 122(3): 366-75. Epub ahead of print 2008

34. Krutzik P O, Clutter M R, Nolan. G P et al. Coordinate analysis of murine immune cell surfacemarkers and intracellular phosphoproteins by flow cytometry. *J Immunol* 2005; 175: 2357-65.

35. Craddock P R, Fehr J, Brigham K L et al. Complement and leukocyte-mediated pulmonary dysfunction in hemodialysis. *N Engl J Med* 1977; 296(14): 769-774.

36. Craddock P R, Fehr J, Dalmasso A P et al. Hemodialysis leukopenia. Pulmonary vascular leukostasis resulting from complement activation by dialyzer cellophane membranes. *J Clin Invest.* 1977; 59(5): 879-888.

37. Kaplow L S, Goffinet J A. Profound neutropenia during the early phase of hemodialysis. *JAMA* 1968; 203(13): 1135-1137.

38. Maugeri N, Brambilla M, Camera M et al. Human polymorphonuclear leukocytes produce and express functional tissue factor upon stimulation. *J Thromb Haemost* 2006; 4: 1323-30.

39. Girardi G, Berman J, Redecha P et al. Complement C5a receptors and neutrophils mediate fetal injury in the antiphospholipid syndrome. *J Clin Invest* 2003; 112: 1644-1654.

40. Redecha P, Tilley R, Tencati M et al. Tissue factor: a link between C5a and neutrophil activation in antiphospholipid antibody induced fetal injury. *Blood* 2007; 110(7): 2423-31.

41. Chazan J A, London M R, Pono L M. Long-term survival of vascular accesses in a large chronic hemodialysis population. *Nephron* 1995; 69: 228-33

42. Smits J H, Linder J, Blankestijn P J et al. Coagulation and hemodialysis access thrombosis. *Nephrol Dial Transplant* 2000; 15: 1755-1760.

43. Jofre R, Rodriguez-Betinez P, Lopez-Gomez J M et al. Inflammatory syndrome in patients on hemodialysis. *J Am Soc Nephrol* 2006; 17: S274-S280.

44. Deppisch R M, Beck W, Goehl H et al. Complement components as uremic toxins and their potential role as mediators of microinflammation. *Kidney Int* 2001; 59, Suppl 78: 271-277.

45. Schmaldienst S, Horl W H. Degranulation of polymorphonuclear leukocytes by dialysis membranes—the mystery clears up? *Nephrol Dial Transplant* 2000; 15: 1909-1910.

46. Rosenkranz A R, Kormoczi G F, Thalhammer F et al. Novel C5a-dependent mechanism of neutrophil stimulation by bioincompatible dialyzer membranes. *J Am Soc Nephrol* 1999; 10: 128-135.

47. Bohler J, Schollmeyer P, Dressel B, et al. Reduction of granulocyte activation during hemodialysis with regional citrate anticoagulation: dissociation of complement activation and neutropenia from neutrophil degranulation. *J Am Soc Nephrol* 1996; 7: 234-241.

48. Mackman N, Tilley R E, Key N S. Role of the extrinsic pathway of blood coagulation in hemostasis and thrombosis. *Arterioscler Thromb Vasc Biol* 2007; 27: 1687-1693.

49. Gorbet M B, Yeo E L, Sefton M V. Flow cytometric study of in vitro neutrophil activation by biomaterials. *J Biomed Mater Res* 1999; 44: 289-97.

50. Zernecke A, Bot I, Djalali-Talab Y et al. Protective role of CXC receptor 4/CXC ligand 12 unveils the importance of neutrophils in atherosclerosis. *Circ Res* 2008; 102: 209-217.

51. Gorbet M B, Sefton M V. Material-induced tissue factor expression but not CD11b upregulation depends on the presence of platelets. *J Biomed Mater Res* 2003; 67A: 792-800.

52. Hong J, Nilson Ekdahl K, Reynolds H et al. A new in vitro model to study interaction between whole blood and biomaterials. Studies of platelet and coagulation activation and the effect of aspirin. *Biomaterials* 1999; 20: 603-11.

53. Gorbet M B, Sefton M V. Expression of procoagulant activities on Leukocytes following contact with polystyrene and PEG grafted polystyrene beads. *J Lab Clin Med* 2001; 137: 345-55.

54. Kario K, Matsuo T, Yamada T et al. Increased tissue factor pathway inhibitor levels in uremic patients on regular hemodialysis. *Thromb Haemost* 1994; 71: 275-9.

55. Cella G, Vertoli U, Naso A et al. Tissue factor pathway inhibitor (TFPI) activity in uremic patients during hemodialysis. *Thromb Res* 1996; 81: 671-7.

56. Zemanova P, Opatrny K, Vit L et al. Tissue Factor, Its Inhibitor, and the Thrombogenicity of Two New Synthetic Membranes. *Artificial Organs* 2005; 29(8): 651-657.

57. Maderna P, Coleman P, Godson C et al. Serum from Hemodialysis Patients Inhibits Basal and Cytokine-Stimulated Tissue Factor Expression in Vitro. *J Am Soc Nephrol* 1999; 10: 2403-2406.

58. Adams M J, Irish A B, Watts G F et al. Hypercoagulabolity in chronic kidney disease is associated with coagulation activation but not endothelial function. *Thromb Res* 2008; Epub ahead of print.

59. Jozsi M, Kapus A, Kerekes K et al. Characterization of factor H-related cell membrane molecules expressed by human B lymphocytes and neutrophil granulocytes. *Immunology Letters* 2001; 77: 55-62

60. Horl W H, Feinstein E I, Wanner C et al. Plasma levels of main granulocyte components during hemodialysis. Comparison of new and reused dialyzers. *Am J Nephrol* 1990; 10 (1): 53-57.

61. Skubitz K M, Craddock P R. Reversal of hemodialysis granulocytopenia and pulmonary leukostasis. A clinical manifestation of selective downregulation of granulocyte responses to C5adesarg. *J Clin Invest* 1981; 67: 1383-1391

62. Ward P A. The dark side of C5a in sepsis. *Nat Rev Immunol* 2004; 4: 133-142.

63. Guo R F, Ward P A. Role of C5a in inflammatory responses. *Ann Rev Immunol* 2005; 23: 821-852.

64. Wolberg A S, Roubey R A. Mechanisms of autoantibody-induced monocyte tissue factor expression. *Thromb Res* 2004; 114: 391-396.

The present invention is not limited to the embodiments described and exemplified above, but is capable of variation and modification within the scope of the appended claims.

What is claimed:

1. A method for reducing or eliminating biomaterial-induced procoagulant activity in blood subjected to extracorporeal treatment that exposes the blood to the biomaterial, the method comprising treating the blood, or the biomaterial, or both, with a complement inhibitor in an amount effective to reduce or prevent C5a/C5aR-mediated tissue factor (TF) formation, thereby reducing or eliminating the biomaterial-induced procoagulant activity in the blood.

2. The method of claim 1, wherein the complement inhibitor comprises one or more of a C5a inhibitor, a C5aR inhibitor, a C3 inhibitor, a factor D inhibitor, a factor B inhibitor, a C4 inhibitor, a C1q inhibitor, or any combination thereof.

3. The method of claim 2, wherein the complement inhibitor is a C5a inhibitor or a C5aR inhibitor.

4. The method of claim 3, wherein the C5a inhibitor or C5aR inhibitor is acetyl-Phe-[Orn-Pro-D-cyclohexylalanine-Trp-Arg] (PMX-53), PMX-53 analogs, neutrazumab, TNX-558, eculizumab, pexelizumab or ARC1905, or any combination thereof.

5. The method of claim 2, wherein the complement inhibitor is a C3 inhibitor.

6. The method of claim 5, wherein the C3 inhibitor is compstatin, a compstatin analog, a compstatin peptidomimetic, a compstatin derivative, or any combinations thereof.

7. The method of claim 2, wherein the complement inhibitor is a C4 inhibitor.

8. The method of claim 1 wherein the extracorporeal treatment of blood comprises hemodialysis.

9. The method of claim 8, wherein the biomaterial comprises hemodialysis filter fibers.

10. The method of claim 8, wherein the blood is from an individual with renal disease.

11. The method of claim 10, wherein the renal disease is end stage renal disease (ESDR).

12. The method of claim 1, wherein the blood is contacted with the complement inhibitor prior to and/or during the extracorporeal treatment.

13. The method of claim 1, wherein the biomaterial is contacted with the complement inhibitor prior to the extracorporeal treatment.

14. The method of claim 1, wherein the complement inhibitor treatment is used together or concurrently with, or sequentially before or after, at least one other anti-coagulant or anti-inflammatory treatment of the blood.

15. A kit comprising a complement inhibitor and a biomaterial for use in an extracorporeal treatment device, and, optionally, instructions for using the complement inhibitor in a method such as the one described above.

16. The kit of claim 15, comprising hemodialysis filtration fibers.

17. An extracorporeal treatment device that includes a complement inhibitor-treated biomaterial, or a biomaterial adapted for or amenable to treatment with a complement inhibitor.

18. The device of claim 17, which is a hemodialysis unit.

* * * * *

UNITED STATES PATENT AND TRADEMARK OFFICE
CERTIFICATE OF CORRECTION

| | | |
|---|---|---|
| PATENT NO. | : 8,445,190 B2 | Page 1 of 1 |
| APPLICATION NO. | : 13/121396 | |
| DATED | : May 21, 2013 | |
| INVENTOR(S) | : John D. Lambris and Konstantinos Ritis | |

It is certified that error appears in the above-identified patent and that said Letters Patent is hereby corrected as shown below:

In the Specifications
Column 1, lines 6-10, the phrase "Pursuant to 35 U.S.C. §202(c), it is acknowledged that the United States government may have certain rights in the invention described herein, which was made in part with funds from the National Institutes of Health under Grant Nos. AL068730 and GM-62134." should read --This invention was made with government support under grant number GM062134 and AI068730 awarded by the National Institute of Health. The government has certain rights in the invention--.

Signed and Sealed this
Twentieth Day of May, 2014

Michelle K. Lee
*Deputy Director of the United States Patent and Trademark Office*

SEQUENCE LISTING

<160> NUMBER OF SEQ ID NOS: 5

<210> SEQ ID NO 1
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (2)..(12)

<400> SEQUENCE: 1

Ile Cys Val Val Gln Asp Trp Gly His His Arg Cys Thr
1               5                   10

<210> SEQ ID NO 2
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is Gly or is missing
<220> FEATURE:
<221> NAME/KEY: VARIANT
<222> LOCATION: (2)..(2)
<223> OTHER INFORMATION: Xaa is Ile, Val, Leu, Ac-Ile, Ac-Val or Ac-Leu
<220> FEATURE:
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Xaa is Trp or an analog of Trp
<220> FEATURE:
<221> NAME/KEY: VARIANT
<222> LOCATION: (10)..(10)
<223> OTHER INFORMATION: Xaa is His, Ala, Phe or Trp
<220> FEATURE:
<221> NAME/KEY: VARIANT
<222> LOCATION: (14)..(14)
<223> OTHER INFORMATION: Xaa is L-Thr, D-Thr, Ile, Val or Gly
<220> FEATURE:
<221> NAME/KEY: VARIANT
<222> LOCATION: (15)..(15)
<223> OTHER INFORMATION: Xaa is Asn or Ala, or is missing
<220> FEATURE:
<221> NAME/KEY: VARIANT
<222> LOCATION: (16)..(16)
<223> OTHER INFORMATION: Xaa is Asn, or is missing

<400> SEQUENCE: 2

Xaa Xaa Cys Val Xaa Gln Asp Trp Gly Xaa His Arg Cys Xaa Xaa Xaa
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is Gly or is missing
<220> FEATURE:
<221> NAME/KEY: VARIANT
<222> LOCATION: (2)..(2)
<223> OTHER INFORMATION: Xaa is Ile, Val, Leu, Ac-Ile, Ac-Val or Ac-Leu
<220> FEATURE:

```
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Xaa is Trp or an analog of Trp
<220> FEATURE:
<221> NAME/KEY: VARIANT
<222> LOCATION: (8)..(8)
<223> OTHER INFORMATION: Xaa is Trp or an analog of Trp
<220> FEATURE:
<221> NAME/KEY: VARIANT
<222> LOCATION: (10)..(10)
<223> OTHER INFORMATION: Xaa is His, Ala, Phe or Trp
<220> FEATURE:
<221> NAME/KEY: VARIANT
<222> LOCATION: (14)..(14)
<223> OTHER INFORMATION: Xaa is L-Thr, D-Thr, Ile, Val or Gly
<220> FEATURE:
<221> NAME/KEY: VARIANT
<222> LOCATION: (15)..(15)
<223> OTHER INFORMATION: Xaa is Asn or Ala, or is missing
<220> FEATURE:
<221> NAME/KEY: VARIANT
<222> LOCATION: (16)..(16)
<223> OTHER INFORMATION: Xaa is Asn, or is missing

<400> SEQUENCE: 3

Xaa Xaa Cys Val Xaa Gln Asp Xaa Gly Xaa His Arg Cys Xaa Xaa Xaa
1               5                   10                  15

<210> SEQ ID NO 4
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: 1-methyl Tryptophan
<220> FEATURE:
<221> NAME/KEY: MOD_RES
<222> LOCATION: (13)..(13)
<223> OTHER INFORMATION: AMIDATION

<400> SEQUENCE: 4

Ile Cys Val Trp Gln Asp Trp Gly Ala His Arg Cys Thr
1               5                   10

<210> SEQ ID NO 5
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (3)..(3)
<223> OTHER INFORMATION: N-methyl Glycine
<220> FEATURE:
<221> NAME/KEY: MOD_RES
```

```
-continued

<222> LOCATION: (4)..(4)
<223> OTHER INFORMATION: 1-methyl Tryptophan
<220> FEATURE:
<221> NAME/KEY: MOD_RES
<222> LOCATION: (13)..(13)
<223> OTHER INFORMATION: AMIDATION

<400> SEQUENCE: 5

Ile Cys Gly Trp Gln Asp Trp Gly Ala His Arg Cys Thr
1               5                   10
```